(12) United States Patent
DeLack

(10) Patent No.: US 9,364,474 B2
(45) Date of Patent: *Jun. 14, 2016

(54) METHOD FOR TREATMENT OF NEUROLOGIC DYSFUNCTION

(71) Applicant: MedDEV, Inc., Stanwood, WA (US)

(72) Inventor: Elaine A. DeLack, Stanwood, WA (US)

(73) Assignee: MedDEV Inc., Stanwood, WA (US)

( * ) Notice: Subject to any disclaimer, the term of this patent is extended or adjusted under 35 U.S.C. 154(b) by 17 days.

This patent is subject to a terminal disclaimer.

(21) Appl. No.: 13/986,573

(22) Filed: May 14, 2013

(65) Prior Publication Data

US 2014/0018382 A1 Jan. 16, 2014

Related U.S. Application Data

(63) Continuation-in-part of application No. 12/657,052, filed on Jan. 12, 2010, now Pat. No. 8,440,685, which is a continuation-in-part of application No. 11/231,442, filed on Sep. 20, 2005, now Pat. No. 7,645,766.

(60) Provisional application No. 60/611,666, filed on Sep. 20, 2004, provisional application No. 61/278,068, filed on Oct. 1, 2009, provisional application No. 61/278,195, filed on Oct. 1, 2009.

(51) Int. Cl.
| | |
|---|---|
| *A61K 31/475* | (2006.01) |
| *A61K 9/00* | (2006.01) |
| *A61K 9/70* | (2006.01) |
| *A61K 31/40* | (2006.01) |
| *C07D 471/14* | (2006.01) |
| *A61K 31/44* | (2006.01) |
| *A61K 31/522* | (2006.01) |

(52) U.S. Cl.
CPC .............. *A61K 31/475* (2013.01); *A61K 31/40* (2013.01); *A61K 31/44* (2013.01); *A61K 31/522* (2013.01); *C07D 471/14* (2013.01); *A61K 9/0014* (2013.01); *A61K 9/7015* (2013.01); *A61K 9/7023* (2013.01)

(58) Field of Classification Search
CPC ... A61K 31/475; A61K 31/40; A61K 9/0014; A61K 9/7015; A61K 9/7023; C07D 471/14
See application file for complete search history.

(56) References Cited

U.S. PATENT DOCUMENTS

| | | |
|---|---|---|
| 3,961,060 A | 6/1976 | Fuxe |
| 7,645,766 B1 * | 1/2010 | DeLack ......... 514/280 |
| 8,440,685 B1 * | 5/2013 | DeLack ......... 514/280 |
| 2003/0113309 A1 * | 6/2003 | Delack ......... 424/94.5 |

OTHER PUBLICATIONS

Ghaziuddin et al. (2002, Journal of Autism and Developmental Disorders, vol. 32, No. 4, pp. 299-306).*
New Respen-A disc that will be replacing Respen-A blended chord disc (Dec. 17, 2012).*
New: Respen-A™ Blended Chord (Jul. 1, 2011).*
New Treatment for Autism "Holds Promise" (May 13, 2010).*
Lamson et al. 2001, Alternative Medicine Review, 6(3), pp. 311-313.*
Puglia et al. 2001, International Journal of Pharmaceutics, 228: 79-87.*
Autism Information Center website www.cdc.gov/ncbddd/autism/faq, Jan. 30, 2008.
Autism website, Updated: Jul. 14, 2006, http://autism.abot.com/od/treatmentoptions/n/drugtreatments.htm.
Yidong B. et al., Resotration of Mitochondrial Function in Cells with Complex I Deficiency, Ann. N.Y. Acad. Sci. 1042:25-35, 2005 doi: 10.1196/annals1338.003.
Baumann, P.A. et al., Negative Feedback Control of Seratonin Release in vivo: Comparison of . . . , Neuroscience vol. 11, No. 1, pp. 195-204, 1984.
Ben-Shachar, D. et al., Neuroanatomical Pattern of Mitochondrial Complex I Pathology Varies between Schizophrenia . . . , PloS ONE website www.plosone.org.
Brummett, B. et al., HP Axis function in male caregivers: effect of the monoamine . . . , Biol. Psychol. 79(2): 250-255, Oct. 2008.
Brummett, B. et al., Lipid levels are associated with a regulatory polymorphism . . . , Med. Sci. Monit., 14(2): CR57-CR61, Feb. 2008.
Cakala, M. et al., Inhibition of mitochondrial complex II dopamine metabolism . . . , Folia Neuropathol, 44(4): 238-243, 2006.
Cohen, I.L. et al., Association of autism severity with a monoamine oxidase A . . . , Clin. Genet. 64: 190-197, 2003.
Courchesne, E. et al., Evidence of Brain Overgrowth in First Year of Life in Autism, JAMA, 290(3): 337-344, 2003.
Craig, I., The role of monoamine oxidase A. MAOA, in the aeti, Novartis Foundation Symposium, Vo. 268, 22-37, 2005.
Davis, L. et al., Cortical Enlargement in Autism is Associated with a Functional VNTR . . . , Am. J. Med. Genet. B Neuropsychiatr Genet. 147B(7): 1145-1151, 2008.
Demily, C., How to differentiate schizophrenia from bipolar disorder using cognitive assessment, Encephale, 35(2): 139-45, Apr. 2009.
Dharia, S. et al., Adrenal Androgens and Aging, Seminars in Rproductive Medicine, vol. 22(4), 361-368, 2004.

(Continued)

*Primary Examiner* — Kara R McMillian
(74) *Attorney, Agent, or Firm* — Todd N. Hathaway

(57) ABSTRACT

A method for treatment of the symptoms of neurologic dysfunctions, including major depression, an autism spectrum disorder (ASD), and schizophrenia. The patient is administered an amount of a compound that increases the catalytic activity of MAO-A. The effective compound is preferably reserpine, administered in a dosage of less than about 0.03 mg per day. The reserpine may be administered topically or transdermally at a dosage in the range from about 0.002 mg per day to about 0.02 mg per day. In homeopathic use, the reserpine may be administered in the form of a homeopathic dilution, preferably as a 12 C homeopathic dilution of reserpine.

3 Claims, 6 Drawing Sheets

(56) References Cited

OTHER PUBLICATIONS

Dosman, C. et al., Children With Autism: Effect of Iron Supplementation on Sleep and Ferritin, Pediatric Neurology, vol. 36(3), pp. 152-158.
Dziobek, I., et al., Hypercholesterolemia in Asperger syndrome: Independence from lifestyle . . . , Psychiatry Research 149, pp. 321-324, 2007.
Gattaz, P. et al., CSF monoamine metaboliltes in schizophrenia patients, Acta psychiat. scand., vol. 66, 350-360, 1982.
Gillberg, C. et al., CSF Monoamines in Autistic Syndromes and other Pervasive Developmental . . . , British J. of Psychiatry, vol. 151, 89-94, 1987.
Gluck, M. et al., Inhibition of brain mitochondrial respiration by dopamine and its metabolites . . . , J. of Neurochemistry, vol. 91, 788-795, 2004.
Harper A. et al., Changes in adrenocortical functions with aging and . . . , Seminars in Reproductive Endocrinology, vol. 17(4), 327-338, 1999.
Heron, P. et al., Paradoxical effects of copper and manganese on brain mitochondrial function, Life Sciences, Vo. 68, 1575-1583, 2001.
Hoshino, Y. et al., The Diurnal Vairation and Response to Dexamethasone Supression Test of Saliva Cortisol . . . , Japanese J. of Pschiatry and Neurology, vol. 41, No. 2, 1987.
Hranilovic, D. et al., Hyperserotonemia in Adults with Autistic Disorder, J. Autism Dev. Discord, 36: 134-1940, 2007.
Hu, R. et al., Changes in brain monoamine neurotransmitter in iron deficiency nonanemic rats, Zhonghua Yu Fang Yi Zue Za Zhi, 30(6): 351-3, 1996.
Insel, B.J. et al., Maternal Iron Deficiency and the Risk of Schizophrenia in Offspring, Arch Gen Psychiatry, vol. 65(10), 1136-1144, 2008.
Jabbi, M. et al., Convergent genetic modulation of the endrocrine stress response . . . , Molecular Psychiatry, Vo. 12, 483-490, 2007.
Jorgensen, H., Studies on the neuroendocrine role of seretonin, Danish Medical Bulletin, vol. 54(4), 266-288, 2007.
Jorgensen, H. et al., Serotonergic Stimulation of Coricotropin-Releasing Hormone . . . , J. of Neuroendocrinology, Vo. 14, 788-795, 2002.
Kuloglu, M., Serum iron levels in schizophrenic patients with or without akathisia, European Neuropsychopharmacology vol. 13, 67-71, 2003.
Lake, C.R. et al., Increase norepinephrine Levels and Decreased Dopamine . . . , Arch Gen Psychiatry, vol. 34, 553-556, 1977.
Contini, V. et al., MAOA-uVNTR Polymorphism in a Brazilian Sample . . . , American J. of Medical Genetics Part B., vol. 141B, 305-308, 2006.
Lake, C.R. et al., Schizoaffective disorder merges schizophrenia and bipolar disorders as one disease . . . , Current opinion in Psychiatry, vol. 20, 365-379, 2007.
Larsson, L.G. et al., Different effects on the responses of functional pre-and postsynaptic 5-HT . . . , Neuropharmacology, vol. 29(2), 85-91, 1990.
Launay, J.M. et al., Serotonin Metabolism and Other Biochemical Parameters in Infantile Autism, Neuropsychobiology vol. 20, 1-11, 1988.
Lehman, E. et al., The Use of Reserpine in Autistic Children, J. of Nervous and Mental Disease, Vo. 125(3), 351-356, 1957.
Ma, Z. et al., Characterization of serotonin-toxicity syndrome (toxidrome) elicited by . . . , European J of Pharmacology, vol. 588, 198-206, 2008.
Macready, N. Promising New Antipsychotics for pediatric Patents . . . , Clinical Psychiatry News, 2001.
Marinovic-Curin, J. et al., Slower cortisol response during ACTH stimulation test in autistic children, Eur Child Adolesc Psychiatry, Vo. 17, 39-43, 2008.
Marinovic-Curin, J. et al., Lower Cortisol and High ACTH Levels in Individuals with Autism, J of Autism and Develpmental Disorders, vol. 33(4), 443-448, 2003.
McNamara, I.M. et al., Further studies in the developmental hyperserotonemia model (DHS) of autism . . . , Brain Research, vol. 1189, 203-214, 2008.
Moore, J.N.P. et al., Trial of reserpine in treatment of schizophrenia, British Medical Journal, 8-14, 1957.
Popova, N.K. et al., MAO A knockout attenuates adrenocortical response to various kinds of stress, Psychoneuroendocrinology, vol. 31, 179-186, 2006.
Rossignol, D.A. et al., The effects of hyperbaric oxygen therapy on oxidative stress . . . , BMC Pediatrics, vol. 7(36), 2007.
Sandman, C.A. et al., Disregulation of proopiomelanocortin and contagious maladaptive behavior, Regulatory Peptides, vol. 108, 179-185, 2202.
Shepherd, M. et al., A controlled clinical study of chlorpromazine and reserpine in chronic schizophrenia, J Neurol. Neurosurg. Psychiat., vol. 19, 232-235, 1956.
Strous, R.D. et al., Lowered DHEA-S plasma levels in adult individuals with autistic disorder, European Neuropsychopharmacology, vol. 15, 305-309, 2005.
Thatcher, R.W. et al., Sensitivity and specificity of an EEG normative database . . . , J. Neurotherapy, vol. 7(3/4), 87-121, 2003.
Vijayalakshmi, V. et al., Effect of resperpine on the monoamine oxidase (MAO) activity in rat liver and brain, Biochemical Pharmacology, vol. 27, 1985-1986, 1978.
Youdim, M.B.H. et al., Activation of monoamine oxidase and inhibition of aldehydl dehydrogenase by resperpine, European J of Pharmachology, vol. 4, 105-108, 1968.

* cited by examiner

Serotonin Metabolism in the Nerve Synapse

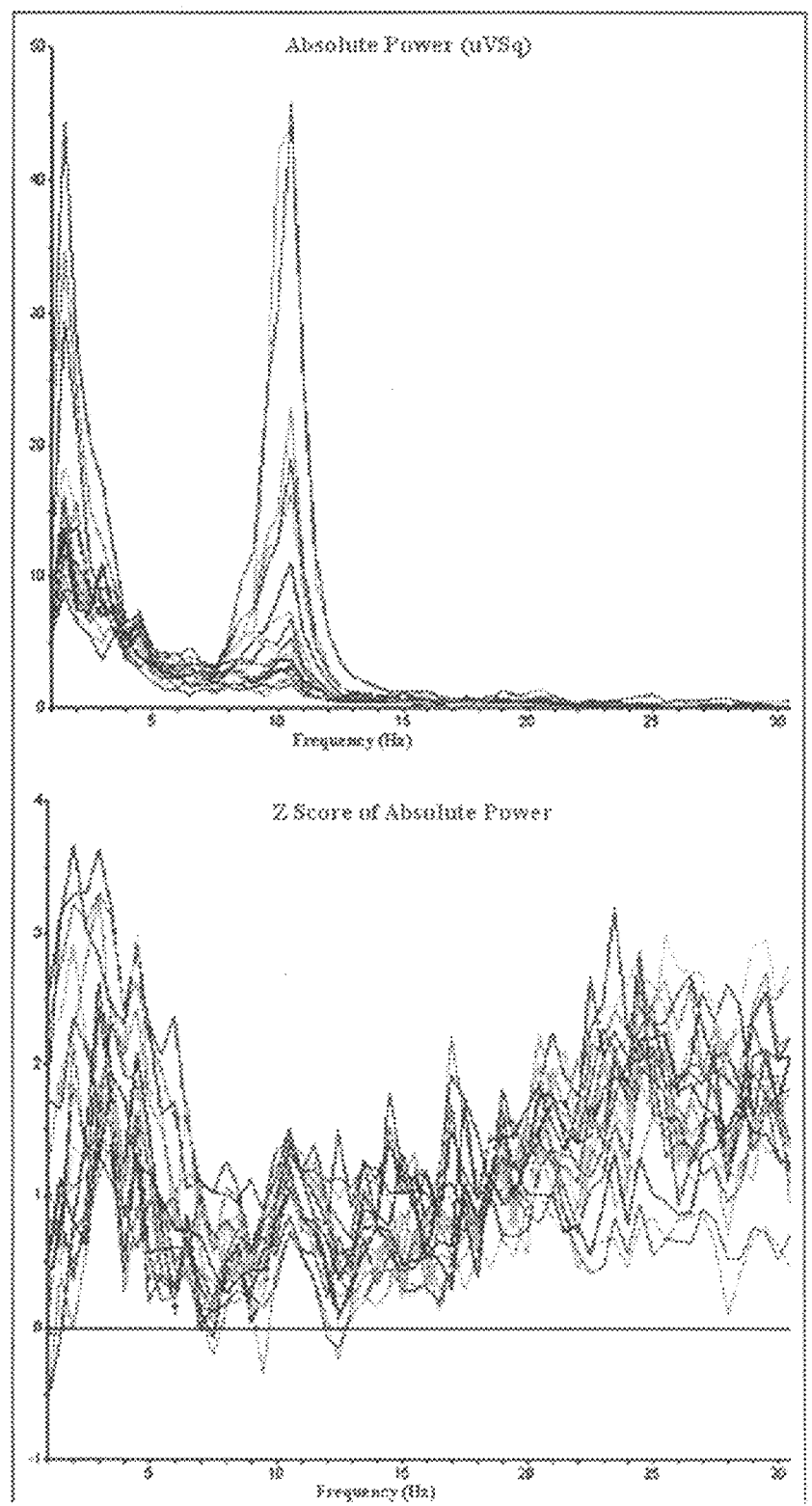
FIG. 5A Fast Fourier Transform Pre Respen Treatment (Transdermal Reserpine 0.01mg)

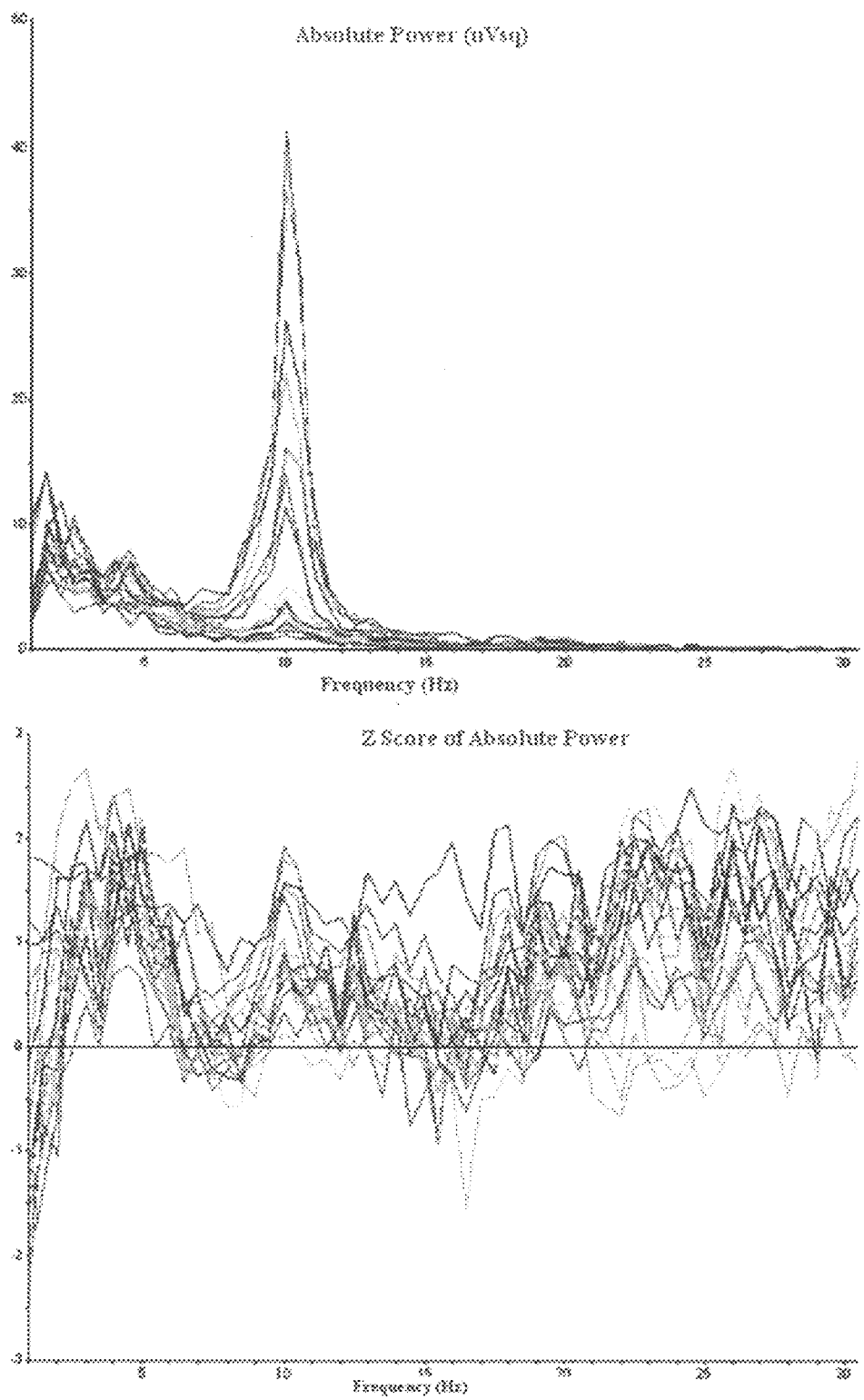
FIG. 4d Fast Fourier Transform Post Respen Treatment
(Transdermal Reserpine 0.01mg)

Figure 6
qEEG before starting HBOT
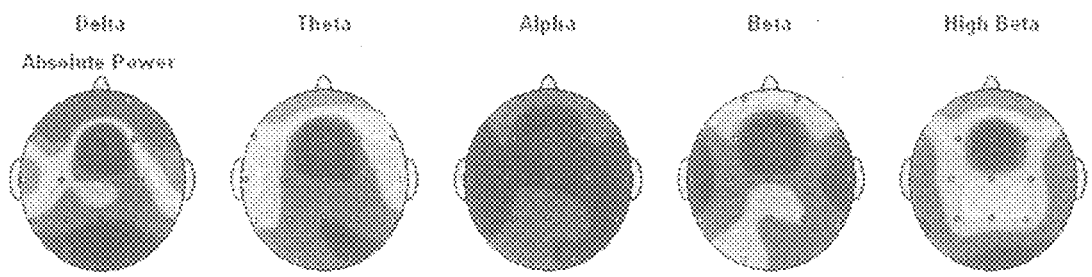
qEEG after 13 sessions of HBOT
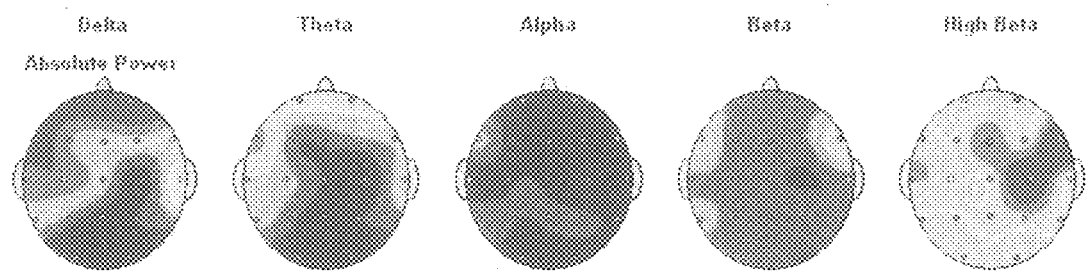
qEEG after 25 sessions of HBOT
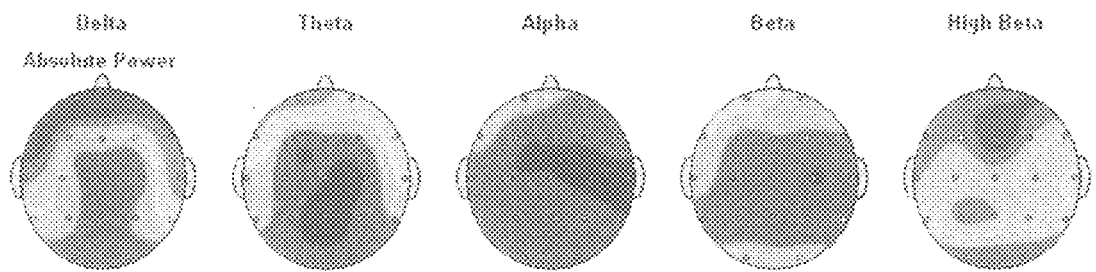
qEEG after 35 HBOT sessions and 3 weeks after beginning Respen treatment
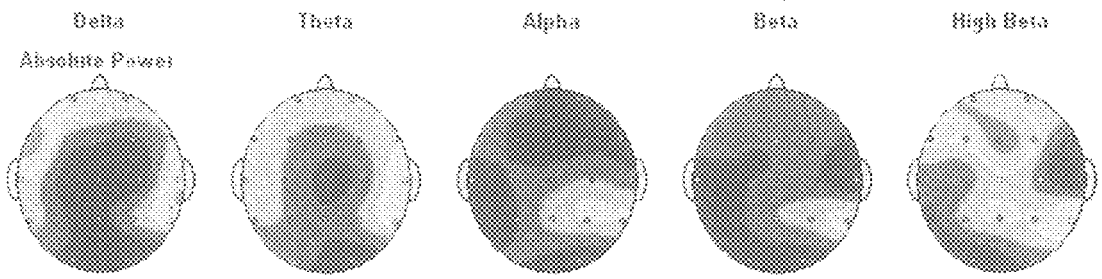

METHOD FOR TREATMENT OF NEUROLOGIC DYSFUNCTION

RELATED APPLICATIONS

This is a continuation-in-part application of U.S. continuation-in-part application Ser. No. 12/657,052 filed on Jan. 12, 2010, which is a continuation-in-part of U.S. Non-Provisional Application Ser. No. 11/231,442 filed on Sep. 20, 2005, entitled "Method and Treatment of Depression and Depressive Mood Disorders" which claims the benefit of U.S. Provisional Patent Application No. 60/611,666 filed on Sep. 20, 2004, and claiming the benefit of U.S. Provisional Applications Ser. Nos. 61/278,068 filed on Oct. 1, 2009 and 61/278, 195 filed on Oct. 1, 2009.

BACKGROUND a. Field of the Invention

The present invention relates generally to the methods for the treatment of neurologic dysfunction, and, more particularly, to methods for treatment of the symptoms of depression, autism spectrum disorder (ASD) and schizophrenic by administration of compositions that serve to increase the activity of Monoamine Oxidase-A (MAO-A).

b. Related Art

It is increasingly recognized that many disorders previously thought to be psychological in nature are, in actuality, to a greater or lesser extent the result of neurologic dysfunction. With respect to the present invention, examples of conditions stemming from what are believed to be neurologic dysfunctions include but are not limited to major depression, autism spectrum disorder (ASD) and schizophrenia.

Major depression is a serious affective disorder (mood disorder). Common symptoms include: persistent sadness; feelings of hopelessness or pessimism; feelings of guilt, worthlessness, helplessness; loss of interest in hobbies and activities that once gave pleasure; decreased energy; memory deficits and difficulty in making decisions and concentrating; insomnia, early morning wakening, or oversleeping; appetite loss and/or weight loss or overeating and weight gain; suicide ideations or attempts, thoughts of death; physical ailments such as headaches, chronic pain or digestive problems that do not respond to treatment. These symptoms can range from mild to severe, but persist for two weeks or more and often interfere with a person's daily functioning.

According to the National Institute of Mental Health, about 18 million Americans are afflicted with major depression annually. It has been estimated to be the second leading cause of disability, surpassed only by heart disease. Depression is about twice as prevalent in women than men and its occurrence is about two to three times more common in first degree relatives of depressed persons.

The causes of depression have not been conclusively identified, but it has heretofore generally been believed that depression is a result of inadequate levels of the neurotransmitters, serotonin and norepinephrine, with most emphasis on the former. Prior efforts at treatment of depression have thus concentrated on increasing the levels of serotonin and/or norepinephrine: Past and current antidepressant treatments have consisted of primarily monoamine oxidase inhibitors, tricyclic antidepressants, and serotonin reuptake inhibitors. All of these treatments have been believed to function by increasing the amount of serotonin in nerve synapses (e.g., Sigma-Aldrich, 2003).

The first antidepressant therapies were monoamine oxidase inhibitors (MAO inhibitors) such as iproniazid. Monoamine oxidase has two subtypes, A and B. Monoamine oxidase A (MAO-A) metabolizes both norepinephrine and serotonin. Thus, it has been believed that the antidepressant effect of MAO inhibitors is the result of increased levels of serotonin and norepinephrine due to the MAO inhibitors blocking the breakdown of these neurotransmitters. Despite the proven efficacy of the MAO inhibitors as antidepressants, their use today has become very limited due to the serious side effects associated with MAO inhibitors. One of the side effects is hepatoxicity: MAO is a very important amine-oxidizing enzyme in the liver and the brain, and the inactivation of MAO interferes in the breakdown of tyramine (tyramine is a common amine in food and some beverages). MAO inhibitors can consequently cause excessive amounts of tyramine to accumulate in the brain, which can result in a hypertensive crisis or death. Most of the older MAO inhibitors were irreversible non-selective inhibitors meaning that they inhibited both MAO-A and MAO-B and predominantly inhibited the MAO-B. Today there are several reversible selectively specific MAO-A inhibitors being studied or in use outside of the United States: Because of their reversibility they have a short duration of action, and thus are somewhat less apt to result in the inactivation of liver metabolism and the accumulation of tyramine.

Another class of antidepressant is tricyclic antidepressants, such as imipramine. Tricyclic antidepressants inhibit the reuptake of norepinephrine and serotonin by blocking the reuptake transporters, resulting in increased levels of these neurotransmitters in the nerve synapses (synaptic clefts). Because of the increased levels of the norepinephrine in the nerve synapses excessive cardiac stimulation can result. These cardiac arrhythmias can be difficult to treat and be potentially life threatening. These side effects prompted the development of selective serotonin reuptake inhibitors (SSRIs), which are the most commonly used antidepressants today. Although the SSRIs do not result in increased concentrations of norepinephrine and therefore avoid causing cardiac arrhythmias, the elevation in the serotonin in the nerve synapses can cause agitation, restlessness, gastrointestinal distress and sexual side effects all of which are common symptoms of depression (Sigma-Aldrich, 2003).

The clinical success of SSRIs in treating depression has been interpreted as supporting the prevalent hypothesis that the etiology of depression is a serotonin deficiency. However, it is not clear as to how the SSRIs, tricyclic antidepressants, or MAO inhibitors relieve depression since there is a lag of several weeks before any mood-elevating effects are noticed after these treatments are started, despite the rapid increase in the levels of serotonin in the nerve synapses. Furthermore, the elevated concentrations of the serotonin in the nerve synapses have been shown to cause symptoms common in depression (Sigma-Aldrich, 2003). Also, the administration of serotonin or its precursors was markedly less effective or not effective at all when compared to the MAO inhibitors, tricyclic antidepressants, or the SSRIs in depressed persons (Beckmann and Kasper (1983), Fortschr. Neurol. Psychiatr. 511(5): 176-82; Nolen et al, (1985), Br. J. Psychiatry 147.16-22). So the question arises, if depression is due to the deficiency of serotonin, then why isn't the administration of serotonin or its precursors L-tryptophan or 5-Hydroxytryptophan more or at least equally effective as these antidepressant treatments? And if depression is due to the deficiency of serotonin, then why does it take several weeks before any benefit may be seen from these antidepressant therapies, even though increase the concentration of serotonin in the nerve synapses almost immediately upon administration? As will be described below, the present invention is founded on a new hypothesis that offers a possible resolution to these issues.

Autism Spectrum Disorder, also known as Pervasive Developmental Disorders (PDD) encompasses at least five disorders: Autism; Asperger Syndrome; Rett Syndrome; Childhood Disintegrative Disorder; and Pervasive Developmental Disorder Not Otherwise Specified (atypical autism). Childhood autism, also known as autistic disorder or infantile autism is a neuro-developmental condition that is characterized by impairment in social interaction, impairment in communication and restricted or stereotyped patterns of behavior and interest usually manifested before the age of 3 years. Core symptoms of ASD are the following: impaired communications (verbal and/or non-verbal); repetitive movements. Other common symptoms of ASD include: impaired social skills; delayed or unusual speech patterns; hyper or hypo sensitivity to light, sound, crowd and other external stimulation; some degree of fine and gross motor difficulty; repetitive behaviors and ritualized activities; aloofness or disengagement with surrounding environment, inability to handle stress or change in routine or environment; some patients have a degree of mental retardation and one in four develop seizures. The severity of these symptoms is very individualized in persons diagnosed with ASD.

The incidence of ASD has increased dramatically over the last decade and today 1 in 150 children are diagnosed as having ASD (http://www.cdc.gov/ncbddd/autism/faq_prevalence.htm). The cause of ASD still eludes the medical community, but several factors have been implicated such as hereditary, heavy metal toxicity, vaccinations, exposure to high amounts of Pitocin (oxytocin) and/or opioids during birth, food allergies, and vitamin and mineral deficiencies.

Most ASD patients have elevated blood levels of serotonin, norepinephrine, and elevated dopamine metabolism resulting in elevated levels of homovanillic acid (HVA) (Launay et al, 1988; Lake et al, 1977; Hranilovic et al, 2007; Gillberg & Svennerholm, 1987).

Currently only one medication, risperidone, has been approved by the FDA for the symptomatic treatment of irritability in autistic children. Several medications have been used "off-label" to help lessen some of the symptoms associated with ASD, but with limited effectiveness. Some of these medications are antipsychotic medications, antidepressants such as Selective Serotonin Reuptake Inhibitors (SSRIs), alpha adrenergic agonists, anticonvulsants, and stimulants such as Ritalin or Provigil. (http://autism.about.com/od/treatmentoptions/p/drugtreatments.htm)

Reserpine, which as is described below is utilized in a preferred embodiment of the present invention, has been used in the past in connection with ASD, but only in much higher doses than in the present invention. Lehman et al in 1957 studied the effect of Reserpine in Autistic children: The optimal dosage range was determined by starting at 0.2 mg orally three times a day and gradually increased to a maximum daily dose of 9 to 12 mg. The study identified the optimum dose of reserpine to be 3 to 7 mg per day with an average of 5 mg per day, and only while a child's dose was within this optimum dosage range were improvements observed (Lehman et al, 1957). A more recent article states that reserpine in doses of 0.25-1.8 mg/day may be effective in autism. (Macready, June 2001); although this article describes doses less than the optimal doses of 3-7 mg taught by Lehman et al, the 0.25-1.8 mg/day dosage range taught by Macready is still far higher than the dosage range of the present invention. Although showing some positive results, it is believed that the testing in Lehman et al and Macready has met with only limited success due to inaccurate assumptions concerning the neurological connections underlying the disorders, leading to use of excessively high dosages of reserpine. Moreover, the high dosages of reserpine tend to exacerbate the side effects associated with the compound.

Schizophrenia is a chronic disabling brain disorder that affects 1.1 percent of the U.S. population age 18 and older (National Institute of Mental Health, www.nimh.nih.gov/health/topics/schizophrenia/index.shtml).

The common signs and symptoms associated with schizophrenia are hallucinations, hearing voices, belief that thoughts are being broadcast to the world, paranoia that others are plotting harm, delusions, disordered thinking, movement disorders, flat affect, social withdrawal, agitation, aggressive behavior and cognitive deficits. These typical symptoms can be so debilitating that the sufferer of the disorder cannot maintain employment or relationships with others. Schizophrenic patients constitute a large percentage of the nation's homeless population.

Many of the symptoms of schizophrenia are similar to the symptoms of major depression and Bipolar Depressive Disorder as well as Autism Spectrum Disorder (ASD). Epidemiological data are consistent with an individual and familial overlap between Bipolar Depressive Disorder and Schizophrenia. It has been proposed in the literature that the two diseases are on the same continuum with varying levels of severity. (Lake & Hurwitz, 2007; Demily et al, 2009) Moreover, it has been shown that Major Depression, Bipolar Depressive Disorder, and Schizophrenia all have similar mitochondria complex I dysfunction that varies only in the anatomical sites where this deficiency exists (Ben-Shachar & Karry, 2008).

Accordingly, there exists a need for a method for treatment of neurologic dysfunctions relating to Major Depression, Autism Spectrum Disorder (ASD) and Schizophrenia, that approaches the root cause of the disorders in a more direct manner than treatments and therefore provides treatment with a greater degree of effectiveness. Still further, there exists a need for such a method that with reduced negative side effects as compared with prior treatments. Still further, there exists a need for such a method that is easy to implement and can be made available on a widespread basis to the many sufferers of such disorders.

SUMMARY OF THE INVENTION

The present invention addresses the problems cited above, and is a method for treatment of the symptoms of neurologic dysfunction, including major depression, autism spectrum disorder, and schizophrenia. Broadly, the method comprises administering reserpine topically or by transdermal application in an amount of less than about 0.03 mg/day.

In a preferred embodiment, there is a method for treatment of major depression, an autism spectrum disorder or schizophrenia, comprising administering to a patient in need thereof an effective amount of a compound that increases the catalytic activity of MAO-A, the step of administering an effective amount of a compound that increases the catalytic activity of MAO-A comprising administering reserpine as a sole active ingredient by transdermal application at a dosage in the range from about 0.002 mg/day to about 0.02 mg/day. The step of administering reserpine by transdermal application in a dosage in the range from about 0.002 mg/day to about 0.02 mg/day may comprise administering reserpine by transdermal application in an amount of about 0.01 mg/day.

The invention further provides a method for treatment of the symptoms of an autism spectrum disorder (ASD), comprising administering reserpine by transdermal application at a dosage of less than about 0.03 mg/day. The step of administering reserpine transdermally at a dosage of less than about 0.03 mg/day may comprise administering reserpine transdermally at a dosage in the range from about 0.002 mg/day to about 0.02 mg/day. The step of administering reserpine transdermally at a dosage in the range from about 0.002 mg/day to about 0.02 mg/day may comprise administering reserpine transdermally at a dosage in the range from about 0.005 to about 0.01 mg/day.

The invention further provides a method for treatment of the symptoms of schizophrenia, comprising administering reserpine to a patient transdermally at a dosage of less than about 0.03 mg/day. The step of administering reserpine transdermally at a dosage of less than 0.03 mg/day may comprise administering reserpine to a patient transdermally at a dosage in the range from about 0.002 mg/day to about 0.02 mg/day. The step of administering reserpine transdermally at a dosage in the range from about 0.002 mg/day to about 0.02 mg/day may comprise administering reserpine transdermally at a dosage in the range from about 0.005 to about 0.01 mg/day.

The invention also provides a method for treatment of the symptoms of an autism spectrum disorder, comprising administering to a patient a daily dosage of a homeopathic dilution of reserpine. The dosage of a homeopathic dilution of reserpine may be administered at least once per day.

The step of administering to a patient a daily dosage of a homeopathic dilution of reserpine may comprise administering the daily dosage of a homeopathic dilution of reserpine by transdermal application. The homeopathic dilution of reserpine may be a 12 C homeopathic dilution of reserpine. The homeopathic dilution of reserpine may have reserpine as a sole active ingredient.

In a preferred embodiment, the invention provides a method for treatment of the symptoms of an autism spectrum disorder, comprising transdermally administering to a patient a daily dosage of a 12 C homeopathic dilution of reserpine, the homeopathic dilution of reserpine having reserpine as a sole active ingredient.

These and other features are advantages of the present invention will be more fully appreciated from a reading of the following detailed description with reference to the accompanying drawings.

BRIEF DESCRIPTION OF THE DRAWINGS

FIGS. 5A-5B are graphical comparisons of the results of quantitative electroencephalograms of a patient having ASD, one performed prior to and the other three weeks after commencement of treatment in accordance with the present invention; and FIG. 6 is a chart of a Nueroguide 2.5 analysis of quantitative electroencephalogram results for the patient of FIG. 5, showing progression of changes observed at intervals over the three week period after commencing the treatment of the present invention.

DETAILED DESCRIPTION

As will be described in greater detail below, the present invention is postulated on the non-binding theory that the conditions that the methods are directed towards treating are due to neurologic dysfunctions resulting the method directed result to at least a significant extent from deficiency in MAO-A activity. The present invention consequently employs compounds that act to increase catalytic MAO-A activity, preferably reserpine and reserpine analogues.

Aspects of the hypothesis and the method of treatment particular to the exemplary dysfunctions of (a) Major Depression, (b) Autism Spectrum Disorder, and (c) Schizophrenia are set forth under the corresponding subheadings below.

a. Depression i. Theoretical Basis

Serotonin is a neurotransmitter. During neurotransmission, serotonin is released from the pre-synaptic neuron into the synapse. It has been heretofore believed that serotonin then travels across the synapse gap and attaches to a specific receptor on the post-synaptic neuron and the nerve transmission is conducted. The present invention is based on an alternative hypothesis, i.e., that it is not the serotonin that activates the post-synaptic receptor, but that instead it is the active metabolite 5-Hydroxyindole acetaldehyde, which is produced within the synapse from the metabolism of serotonin by MAO-A.

Figure 1:
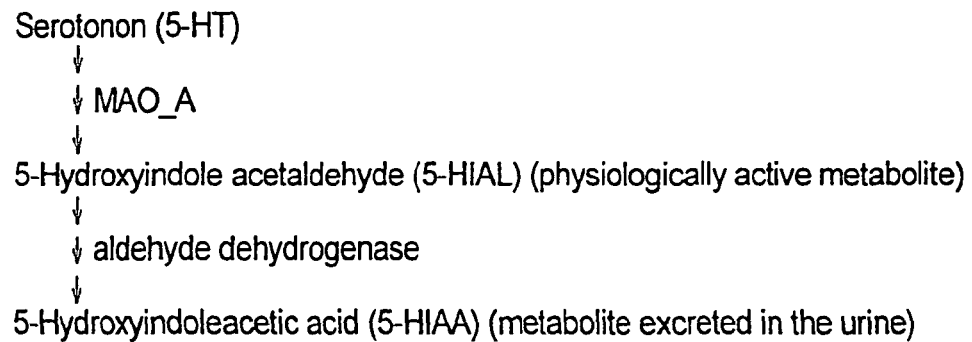
FIG. 1 is a flow diagram showing the phases in serotonin metabolism in the nerve synapse, producing the 5-HIAL active metabolite and the 5-HIAA end metabolite.

As is shown in FIG. 1, serotonin is metabolized by MAO-A into 5-Hydroxyindole acetaldehyde (5-HIAL), which in turn is rapidly metabolized by aldehyde dehydrogenase into 5-Hydroxyindoleacetic acid (5-HIAA), the latter being the major serotonin metabolite that is excreted in the urine. 5-HIAL has been shown to be a physiologically active metabolite, and can activate Long-Term Depression of the cerebellar Purkinje neurons and neurons in the prefrontal cortex (Palmer et al (1986) Alcohol Clin. Exp. Res. 10:682-685). Long-Term Depression of the cerebellar Purkinje neurons and the prefrontal cortex is essential in learning and memory (Ito (1986), Neurosci. Res. 3:531-539). If the cerebellar Long-Term Depression is blocked, the ability to adaptively modify the vestibuloocular reflex is impaired (van Alphen & De Zeeuw (2002), Eur. J. Neurosci 16(3):486-490). Dysregulation of the vestibuloocular system has been correlated with depression, as well as impulsive and autistic personality types (Kornilova et al (1999), Hum. Physiol. 25(5):549-54).

The hypothalamus has serotonin accumulating neurons, capacity to uptake 5-Hydroxytryptophan (5-HTP, a precursor of serotonin), with the ability to decarboxylate 5-HTP into serotonin (5-HT), and marked activity of MAO-A to metabolize serotonin into its metabolites 5-HIAL and 5-HIAA (Sakumoto et al (1984), Brain Res. Bull. 12(6)A:721-33). The hypothalamus is involved in cognitive functions; thyroid function; adrenal cortex function that regulates blood pressure, water balance, cortisol production, steroid hormone production; maintenance of the waking state; appetite regulation; sense of well being; body temperature regulation. Many of the symptoms associated with depression can perhaps be correlated to a hypothalamic dysregulation. The activity of the hypothalamic-pituitary-adrenocortical (HPA) axis is often high in depressive disorders. Depressed patients with high HPA activity tend to have impaired MAO-A metabolism of serotonin and norepinephrine resulting in low levels of the active metabolites (Stokes et al (1987), Am. J. Psychiatry 144(7):868-72.

In view of this evidence, it is believed that the post-synaptic receptor may in fact be activated by the serotonin metabolite 5-HIAL, following the metabolic pathway shown in FIG. 6. Immediately following receptor activation the 5-HIAL is metabolized into 5-HIAA, and which ultimately is excreted in the urine.

By way of verifying this theory, it will be noted that activity of the MAO-A and the 5-HIAL in the serotonin metabolic pathway can be ascertained by measuring the amount of 5-HIAA produced, since the 5-HIAA end metabolite can be easily measured in the cerebral spinal fluid (CSF) or urine of patients. Existing research has shown that the 5-HIAA levels in the CSF of patients with major depression are low, tending to confirm inadequate serotonin metabolism. Furthermore, research by Mann and Malone in 1997 (Biological Psychiatry 41(2):162-171) revealed that the CSF 5-HIAA was significantly lower in depressed patients involved in high-lethality suicide attempts than in the depressed patients having a history of low-lethality suicide attempts. Numerous research studies, conducted in various countries, have yielded similar findings that self-destructive behaviors are associated with low levels of 5-HIAA in the CSF (e.g., Brown & Linnoila (1990), Journal of Clinical Psychology 51:Supplement 31-41; van Praag (1986) Suicide Life Threat Behavior 16(2): 103-132). The prevalent belief, however, has been that the low levels of the serotonin metabolite 5-HIAA observed in depressed patients are due to inadequate levels of serotonin in the nerve synapse; by contrast, in the present invention it is hypothesized that these low levels of 5-HIAA are not due to inadequate levels of serotonin itself, but rather to inadequate metabolism of the serotonin.

The effect of daidzin to suppress ethanol intake in ethanol-preferring laboratory hamsters further supports the instant theory, that deficiency of the 5-HIAL active metabolite is a cause of depression and precipitates substance abuse. Daidzin inhibits aldehyde dehydrogenase, which is the enzyme that metabolizes 5-HIAL to 5-HIAA. Daidzin analogues that inhibit aldehyde dehydrogenase, but not the compound that increases MAO-A activity, have demonstrated a potent anti-dipsotropic effect, whereas daidzin analogues that potently inhibited the compound that increases MAO-A activity produced no antidipsotropic effect (Rooke et al (2000), Lancet Journal 1(8385):1048-1049). Furthermore, it has been shown that alcohol consumption inhibits aldehyde dehydrogenase, resulting in increased concentrations of 5-HIAL (Jenkins et al (1984), Lancet 1(8385): 1048-1049). This would appear to explain the pattern of self-medication via alcohol abuse that is commonly observed in patients having depressive disorders.

Research has also shown that a genetic deficiency of the compound that increases MAO-A activity induces major alterations in mood and behavior in animals and humans. Knockout mice lacking the compound that increases MAO-A activity were found to have high levels of extracellular serotonin and, conversely, 40% lower spontaneous firing of the serotonergic neurons in the dorsal raphe nucleus (Evrard et al (2002), Eur. J. of Neurosci. 15(5):841-851). The dorsal raphe nucleus is a major area of the brain affected in depressive disorders. This research supports the present hypothesis that serotonin is not the activator of the receptor on the post-synaptic serotonergic neuron, but rather that the serotonin metabolite 5-HIAL is the activator of the post-synaptic receptor, resulting in the firing of the serotonergic neurons such as in the dorsal raphe nucleus.

Figure 2:
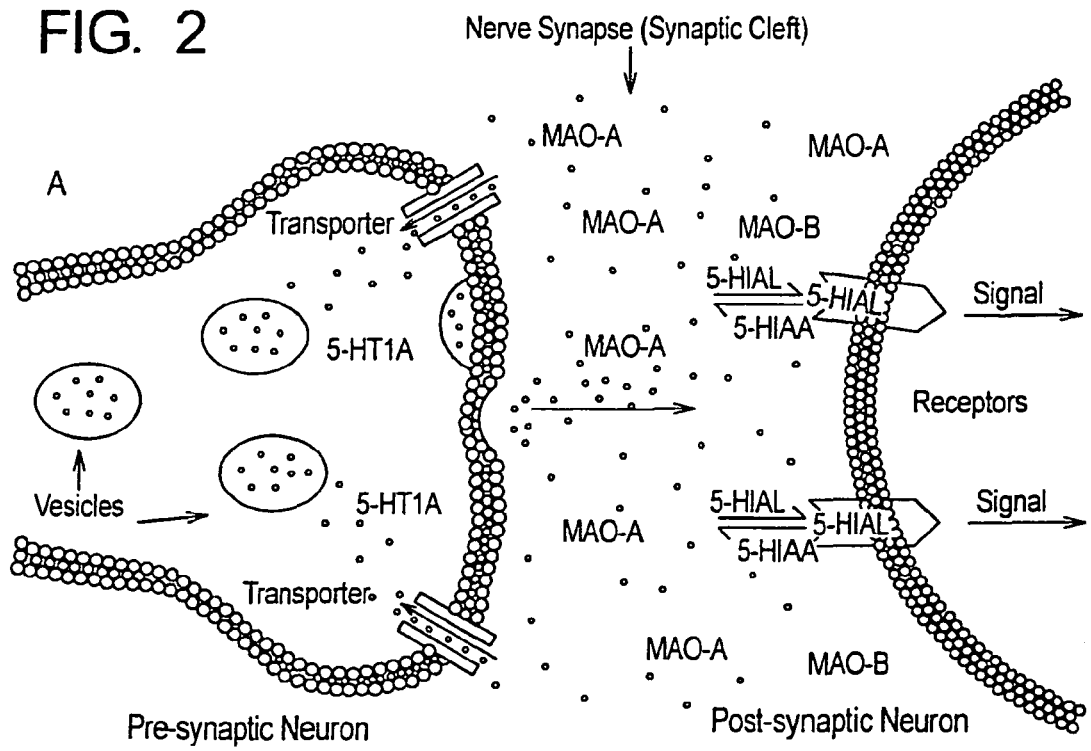
FIG. 2 is a simplified view of a nerve synapse, illustrating the theory on which the treatment of the present invention is based, i.e., that the receptors of the post-synaptic neuron are activated by the 5-HIAL metabolite of serotonin, rather than by the serotonin itself as has been believed in conventional theories.

Accordingly, referring again to FIG. 2, the theory on which the present invention is founded may be stated as follows: During neurotransmission, serotonin is released into the synaptic cleft from storage vesicles present in the pre-synaptic neuron. The serotonin is then metabolized in the synaptic cleft by MAO-A, into the active metabolite 5-HIAL. The 5-HIAL binds to the receptor on the post-synaptic neuron, thereby transferring the signal. The 5-HIAL is then rapidly metabolized by aldehyde dehydrogenase into 5-HIAA, which is eventually excreted in the urine.

Assuming this is correct, depression and other mood disorders may properly be attributed to reduced availability of the 5-HIAL metabolite rather than to low levels of serotonin, as has been previously assumed. The present invention therefore addresses the reduced availability of 5-HIAL by administering to the patient a compound that increases the catalytic activity of MAO-A, thereby increasing metabolism of the serotonin to 5-HIAL. The operative compound is suitably reserpine or a reserpine analogue.

The dose of the reserpine or other operative compound should be sufficient to metabolize the serotonin to 5-HIAL at a rate that prevents elevated concentration of non-metabolized serotonin from developing in the synaptic cleft, as this would result in too much serotonin being bound to the transporter, and would in turn result in the increased activation of 5-HT1A and therefore decreased release of serotonin and inhibition of MAO-A. Yet the dose should not be so high that the synthesis of serotonin is unable to keep up with the turnover rate, as this would deplete the stores of serotonin in the storage vesicles and result in inadequate release of serotonin into the synaptic clef, which in turn would result in inadequate 5-HIAL production and therefore inadequate activation of the post-synaptic neuron. Administering too high of dose of the operative compound consequently results in an undesirable increase in the symptoms of depression, as has in fact been observed, with excessive dosages of reserpine; however, it has been found that these symptoms are rapidly resolved upon decreasing the dosage to levels suitable for the individual patient.

The observed efficacy of the present invention appears to confirm that inducing an increase in the metabolism of serotonin to 5-HIAL has a strongly beneficial effect in treating mood disorders, and has a profoundly more immediate impact than the current antidepressant therapies of MAO inhibitors, tricyclic antidepressants, and serotonin reuptake inhibitors. Furthermore, as noted above, intentionally increasing metabolism of serotonin runs directly contrary to the conventional belief regarding the etiology of depression. Yet, it is incontestable that MAO inhibitors, tricyclic antidepressants, and serotonin reuptake inhibitors also produce significant benefits when treating depression. This apparent contradiction may be explained as follows, making reference to FIGS. 3A-3B and 4A-4B:

Research has shown that MAO inhibitors as well as tricyclic antidepressants (imipramine, clomipramine, amitriptyline, zimeldine, viloxazine, nortriptyline, maprotiline, nomifensine, and doxepine) and some serotonin reuptake inhibitors (fluoxetine, fluvoxamine, citalopram)) demonstrate inhibitory activity towards both MAO-A and MAO-B, but with clearly more potent selectivity for MAO-B. Long-term administration (four weeks or more) of these antidepressants consequently results in a significant increase in the inhibition of MAO-B relative to inhibition of MAO-A. Furthermore, these antidepressants are competitive inhibitors of MAO-A but noncompetitive inhibitors of MAO-B (Egashira et al (1996), Gen. Pharmacology 27(5):773-778; Gnerre et al (2001), J. of Pharm & Pharm. 53(8):1125-1130). Competitive inhibitors have a more reversible effect, in that saturating concentrations of the substrate (such as increased levels of the substrate serotonin or norepinephrine) can remove the inhibition, thus negating the MAO inhibitory effect. Noncompetitive inhibitors, however, are irreversible and do not compete with the natural substrate, so that an increased concentration of the substrate (i.e., serotonin or norepinephrine) does not negate the MAO inhibitory effects.

Figure 3A:
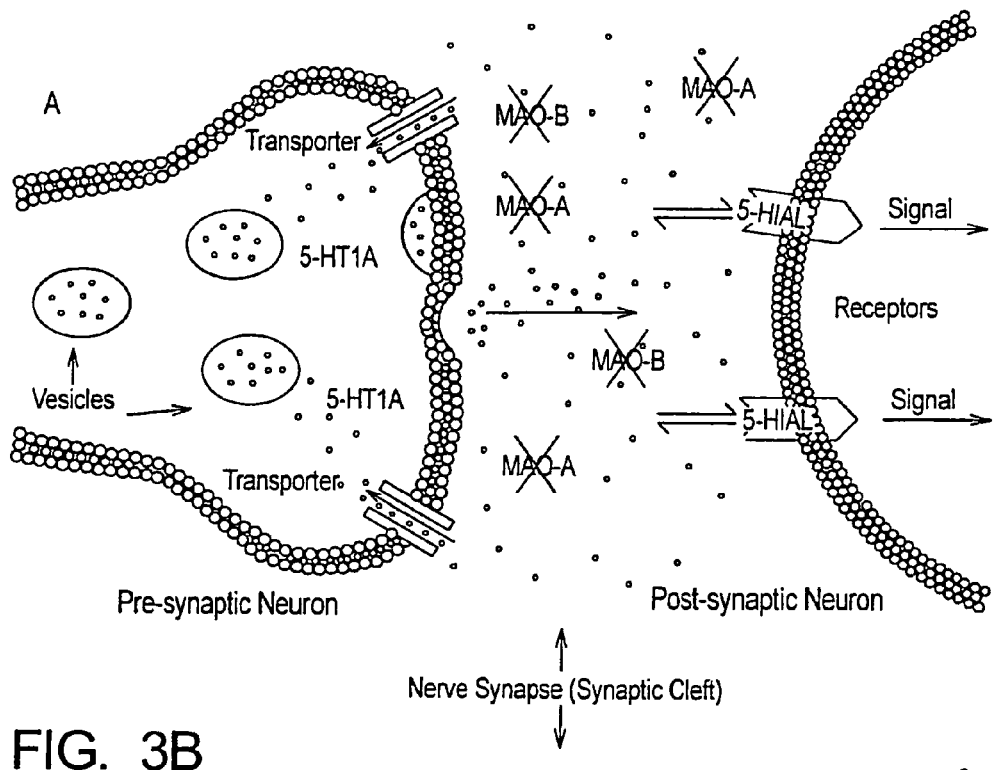
FIGS. 3A-3B are simplified views of a nerve synapse, similar to FIG. 2, illustrating the mechanism of conventional MAO inhibitors, as hypothesized by the inventor herein pursuant to the theory on which the present invention is based.
Figure 3B:
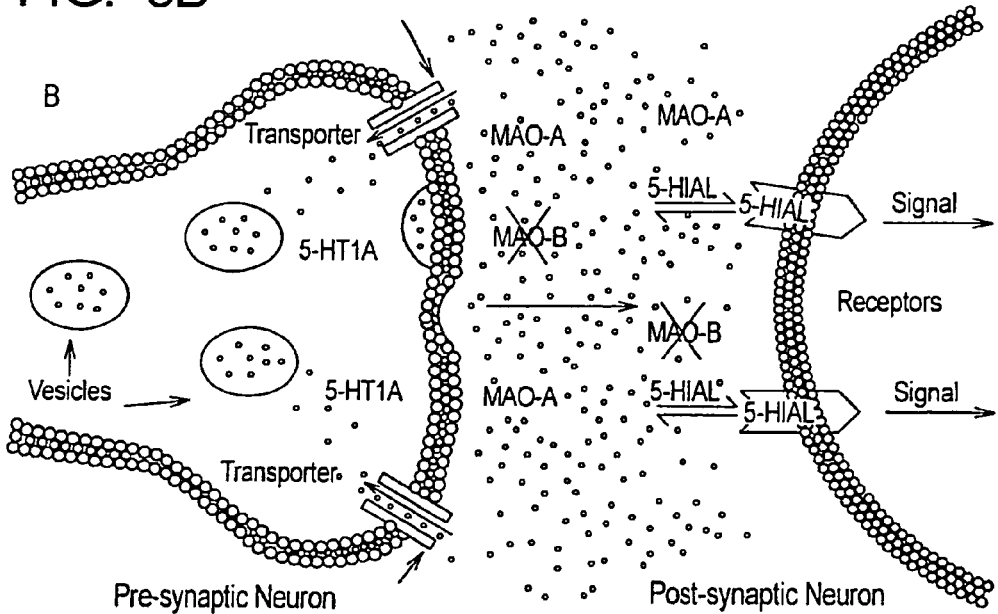

Consequently, as can be seen in FIG. 3A, MAO-A Inhibitors initially inhibit both MAO-A and MAO-B, the inhibition of MAO-A being competitive and that of the MAO-B being noncompetitive as described above. Inhibition of the MAO-A inhibits metabolism of serotonin to 5-HIAL, so that continued release of serotonin from the vesicles of the pre-synaptic neuron results in an increased concentration of serotonin in the synaptic cleft. As can be seen in FIG. 4B, the increased serotonin levels in turn compete with the MAO-A Inhibitor, resulting in a negation of the MAO-A inhibition.

Thus, it is believed that the conventional antidepressants noted above have only a short-acting MAO-A inhibitory effect, because after a few weeks of treatment the concentration of the substrates (serotonin or norepinephrine) increase to the level capable of negating the MAO-A inhibitory effect, while the MAO-B inhibitory effect persists indefinitely. The ultimate result is an increased ratio of MAO-A:MAO-B activity, with the MAO-A being proportionally higher. The increased MAO-A levels, in turn, cause increased metabolism of the serotonin to the metabolite (5-HIAL) that activates the receptors of the post synaptic neurons. This would appear to account for the antidepressant effect of conventional treatments, and may also explain why there is a lag of several weeks before any benefit is seen when using prior antidepressants.

Figure 4A:
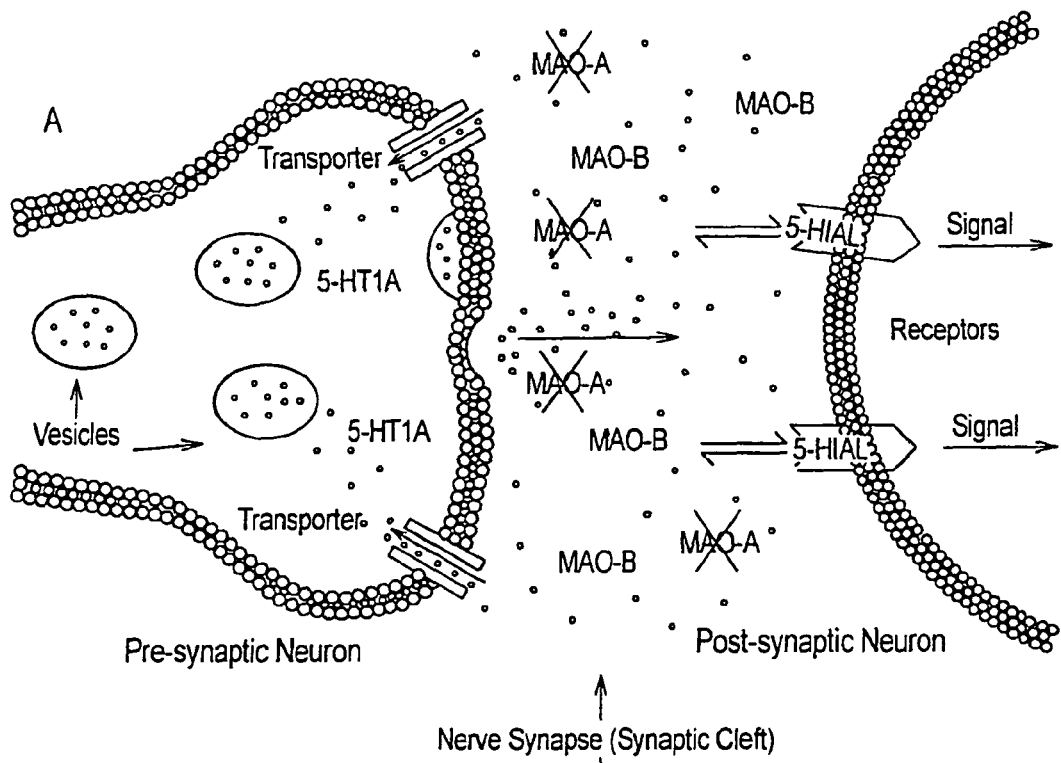
FIGS. 4A-4B are simplified views of a nerve synapse, similar to FIGS. 3A-3B, illustrating the mechanism of conventional selective serotonin reuptake inhibitors (SSRIs), as hypothesized by the inventor herein pursuant to the theory on which the present invention is based.
Figure 4B:
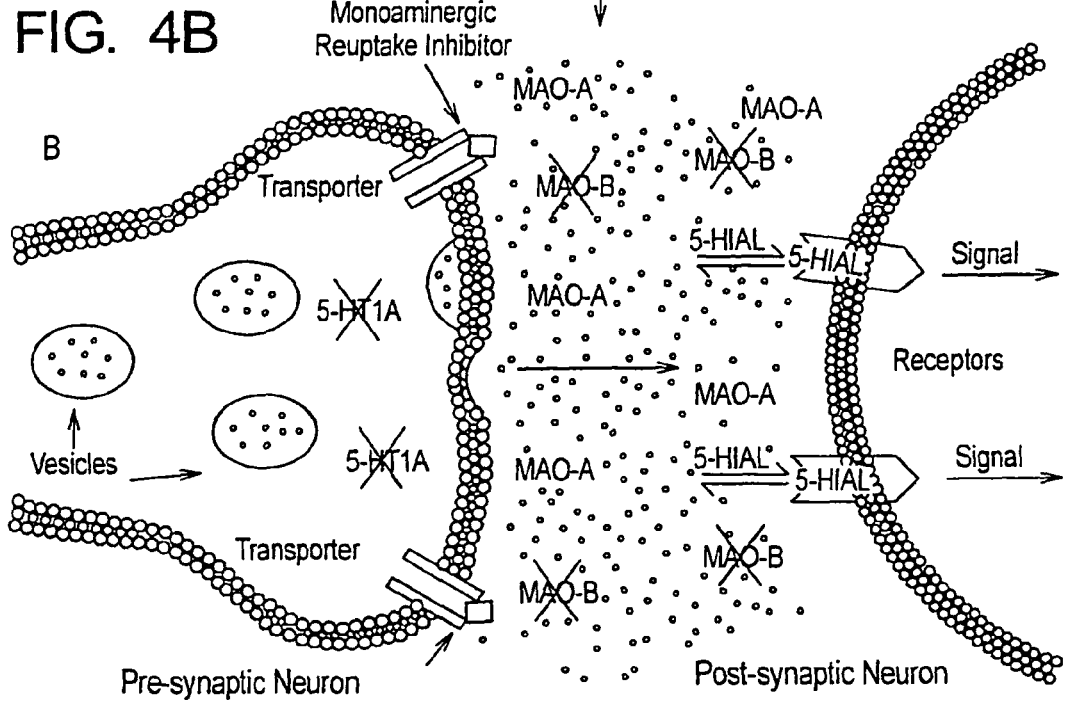

As is shown in FIGS. 4A-4B, the benefits observed with SSRIs and tricyclic antidepressants may in turn be due to the effect of reducing inhibition of the release of serotonin from the pre-synaptic nerve. Inhibition of serotonergic neurons is mediated by 5-HT1A autoreceptors. Serotonin that is not metabolized in the nerve synapse binds to the serotonin transporter, which reuptakes the serotonin from the nerve synapse and carries it back into the presynaptic serotonergic neuron. This serotonin that is taken back up into the presynaptic neuron activates the 5-HT1A autoreceptors in the presynaptic neuron, resulting in a decrease in the release of serotonin into the nerve synapse. The activation of the 5-HT1A autoreceptors, by the reuptake of the serotonin, also induces inhibition of the MAO-A activity, resulting in a decrease in the synapse metabolism of serotonin to the active metabolite 5-HIAL (Larsson et al, 1990).

As shown in FIG. 4B, SSRIs and tricyclic antidepressants block the binding of the serotonin to the serotonin transporter, which in turn prevents the activation of the 5-HT1A autoreceptor. As a result, serotonin continues to be released into the synaptic cleft, from the storage vesicles in the pre-synaptic neuron, despite already elevated levels in the cleft. Furthermore, the metabolism of serotonin into the active 5-HIAL metabolite is inhibited by the SSRIs by competitive inhibition of MAO-A, similar to the effect of the MAO-A inhibitors described above.

The net result is a significant increase in the concentration of serotonin in the synaptic cleft. After a period of delay, the elevated serotonin concentrations induce additional MAO expression, and furthermore the increased concentration of serotonin results in a negation of the MAO-A inhibitory effect of the SSRI. SSRIs (like the MAO inhibitors) are also noncompetitive inhibitors of MAO-B, so that irreversible inhibition of MAO-B also results in an increased ratio of MAO-A: MAO-B activity. These effects become more pronounced the longer the therapy is administered, finally resulting in increased 5-HIAL levels. This would appear to explain the beneficial effects of SSRIs, and why there is again usually a lag of several weeks before such effects are seen.

5-HT1A autoreceptors have been shown to be genetically expressed twofold higher in depressed patients and fourfold higher in completed suicide cases (Lemonde et al (2003), J. of Neurosci. 23(25):8788-8799). Consistent with the above explanations, the known genetic link to expression of the 5-HT1A autoreceptors, coupled with the fact that high levels of estrogen will inhibit MAO-A activity (Youdim et al (1989), FASEB Journ. 4(6):1753-1759; Chevillard et al (1981) Brain Res. 222(1):177-181), may explain the genetic and gender prevalence of depressive disorders. Research has also shown that the ratio of MAO-A:MAO-B activity decreases with age (Fowler et al (1980), J. of Neur. Trans. 49(1-2):1-20), which may explain the prevalence of depression in the elderly.

ii. Method

The present invention provides a method for treatment of depression and other mood disorders, by the application or administration of a compound (which may be referred to for purposes hereof as an MAO-A agonist) that increases the catalytic activity of MAO-A in metabolizing serotonin to its active metabolite 5-HIAL. Suitable compounds includes reserpine and reserpine analogues; as used herein, the term "reserpine analogue" refers to compounds having a pharmacological effect similar to reserpine, in effecting an increase in the catalytic activity of MAO-A. Reserpine in particular has been shown to activate MAO-A, as well as to inhibit aldehyde dehydrogenase (Youdim & Sandler (1968) Eur. J. of Pharm. 4:105-108). It is anticipated that other rauwolfia alkaloids and their analogues may also be useful.

The treatment composition of the present invention may be administered by any suitable means, such as orally, or by transdermal or topical application, or injection, or inhaler, to give just a few examples. However, administration by transdermal or topical application is generally preferred, in that this provides significant advantages in terms of ease of use and more consistent dosage levels.

Accordingly, a preferred composition for use in the treatment of the present invention is formed by the preferred MAO-A agonist reserpine in a transdermal or topical disk or spray. When transdermally or topically administered, daily dosage is significantly less than 0.03 mg/day and preferably within the range of about 0.002-0.02 mg/day, with a range of about 0.006-0.01 mg/day being most preferred. The treatment composition is suitably applied in a single daily dose, e.g., 0.01 mg of the MAO-A agonist in 0.05 ml of transdermal cream applied once every morning. Caffeine may also be included in the composition to compensate for the anti-hypertensive effect of the preferred reserpine; the caffeine may suitably be included in an amount from about 50-100 mg/dose.

As has been explained above, the present invention differs profoundly from previous methods used for treatment of depression. Based on the prior theories and antidepressant treatments, administration of any agent that would enhance the metabolism of serotonin would be strongly contraindicated. Current conventional antidepressant medications are aimed at increasing the levels of serotonin: The MAO inhibitors are aimed at preventing, rather than increasing, metabolism of serotonin, which the tricyclic antidepressants and serotonin reuptake inhibitors are similarly aimed at maintaining higher levels of serotonin in the nerve synapses. The use of a MAO-A agonist therefore runs directly contrary to the purpose of both types of treatment, and even more so against the recent trend toward the use of specific MAO-A inhibitors as a treatment for depression. In point of fact, the drug information reference "Facts and Comparisons 2002" states expressly that reserpine is contraindicated in mental depression, or where there is a history of mental depression, especially with suicidal tendencies.

iii. EXAMPLES

The following illustrative examples relate to actual practice of the invention described above, and its success in alleviating the symptoms of depression and facilitating the cessation of substance abuse.

Example One

A 44-year old, 250-pound male suffering from depression was treated in accordance with the method of the present invention. The patient reported suffering from the following persistent symptoms of depression for four years prior to treatment.

Persistent anxious mood
Feelings of hopelessness, pessimism
Feelings of guilt, worthlessness
Loss of interest or pleasure in hobbies and activities that were once enjoyed
Decreased energy, fatigue
Difficulty concentrating, remembering, making decisions
Insomnia, early-morning awakening, daytime sleeping
Overeating and weight gain
Thoughts of death or suicide
Persistent physical symptoms that do not respond to treatment—headaches and gastric upset
Inability to stop drinking until inebriated if offered alcohol Treatment was in the form of 0.01 mg of reserpine per 0.05 ml of transdermal cream, applied transdermally once a day in the morning. Within four hours of the first application of the treatment, the patient reported a significant improvement in his state of mind, and that the negative outlook and emotions identified above had resolved. The patient has continued on the treatment, and remains free of all of the prior symptoms so long as the consecutive 24-hour dosing regimen is followed. Moreover, he has ceased overeating and has lost in excess of 20 pounds during the treatment. In instances where the patient has forgotten to take the dose for a day, symptoms have begun to return within about 32 hours of the last dose administered (reserpine has a 33 hour therapeutic half-life in the human body). When the dose was missed for 72 hours; the patient displayed agitation, difficulty concentrating, feelings of worthlessness and pessimism; however, within one hour of applying the missed dose, the patient was free of all symptoms. The patient has had an occasional beer or mixed drink while socializing with friends during the treatment, but often has not even finished the drink.

Example Two

A 44-year old, 175-pound female suffering from depression was treated in accordance with the method of the present invention. The patient reported suffering from the following persistent symptoms of depression for 15 years prior to treatment:

Persistent sad mood with frequent episodes of weeping for no reason
Feelings of hopelessness and pessimism
Feelings of helplessness
Decreased energy, fatigue
Difficulty concentrating, remembering, making decisions
Insomnia
Overeating and weight gain
Persistent physical symptoms that do not respond to treatment—headaches, acne, and hair loss.

The treatment consisted of 0.01 mg of reserpine per 0.05 ml of cream, applied transdermally by rubbing the cream into the skin once a day in the morning. Within one hour of applying the dose the patient reported increased energy; she developed a headache and some nausea that persisted for the first eight hours after initiation of the treatment, but then spontaneously resolved. Within 10 hours of the first application the patient reported all perceptible symptoms had resolved, with the exception that she still had some slight problems with memory. The patient continued on the treatment for 30 consecutive days with no return of her symptoms during that time. The patient averaged weight loss of one to two pounds per week during the 30-day course of treatment. The treatment was interrupted for 10 days at the end of the first 30 consecutive-day treatment; all of the symptoms returned during this period of abstinence from the treatment, and the weight loss halted despite no marked change in her diet. The patient then resumed the treatment, and within one hour of doing so she reported that her symptoms had again resolved. She also resumed the 1-2 pound per week weight loss. She lost a total of 15 pounds during the first 50 days, and continues on treatment.

Example Three

A 20-year old, 220-pound male suffering from depression and substance abuse (marijuana use twice a day, and consumption of alcohol to the point of inebriation about twice a week) had tried unsuccessfully to stop the substance abuse several times in the preceding three years. The longest period he was able to abstain from smoking marijuana was two weeks, due to "intense cravings". The patient reported suffering from the following persistent symptoms of depression for 5 years prior to treatment:

Persistent sad and "empty" mood
Feelings of pessimism
Decreased energy
Insomnia
Overeating and weight gain
Thoughts of death but not suicide
Persistent physical symptoms that do not respond to treatment—headaches and stomach cramps The treatment consisted of 0.01 mg of the reserpine per 0.05 ml of cream, applied transdermally by rubbing the cream into the skin once a day in the morning. Within two hours of applying the first dose all of the pessimism and negative mood aspects listed above resolved, and he also reported experiencing no cravings for marijuana or alcohol. On the third day of treatment, the patient reported some feelings of sadness and decreased energy; the dose was then decreased to 0.0075 mg of reserpine, and the symptoms resolved that same day. He has not used any marijuana during the treatment and he reports having no cravings for the substance. He does have an occasional single beer, about twice a month, but he reports no desire to drink alcohol. He lost five pounds during the first 60 days and continues on the treatment.

Example Four

A 64-year old female with a family history of depression and a personal history of major clinical depression, who had been hospitalized in 1975 and again in 1990 with major episodes of depression, including extreme suicidal ideations. Numerous different medications were tried in an effort to stabilize her condition, with only limited success. Since 1990 she had been taking 25 mg to 75 mg of nortriptyline to manage her depression, and reported having to increase the dose to as high as 100 mg during stressful life events. The patient experienced dry mouth and constipation as side effects of using nortriptyline. The patient reported suffering from the following symptoms, despite taking nortriptyline:

Decreased energy, fatigue
Early morning awakening

The patient discontinued the use of nortriptyline and the same day started the treatment of the present invention, using 0.01 mg of the reserpine per 0.05 ml cream, applied transdermally by rubbing the cream into the skin once a day in the morning. Within one hour of applying the first dose the fatigue and loss of energy resolved. She reported increased energy throughout the day and she did not experience tiredness in the evening as per usual on the nortriptyline. Early in the treatment she reported that she was going through a very stressful time in her life, that in the past would have required her to increase her dose of nortriptyline as high as 100 mg in order to cope with the stress, but she has not had to increase the dosage when using the treatment of the present invention. After 10 months of consecutive daily treatment using 0.01 mg of the MAO-A activity stimulator (reserpine) per 0.05 ml cream applied transdermally, with no return of the symptoms listed above, the patient experienced some insomnia and fatigue during a prolonged, very stressful event (a lawsuit). The patient increased the dose to 0.02 mg of the MAO-A activity stimulator for one week, and insomnia and fatigue resolved. After the stressful event was completed, the patient returned to the 0.01 mg dose of the MAO-A activity stimulator, with no return of any symptoms of depression.

Example Five

A 24-year old female weighing 180 pounds with a clinical diagnosis of depression. This patient had been using a serotonin reuptake inhibitor (SSRI) for three months with moderate effect in alleviating her symptoms of depression, with the exception of labile emotions consisting of transient irritability. The patient experienced a 15-pound weight gain while using the serotonin reuptake inhibitor.

Due to the weight gain, the patient had discontinued the use of the serotonin reuptake inhibitor for a period of two months prior to starting the treatment of the present invention. She reported that during this lapse in treatment all of her symptoms of depression had returned, which included:

Insomnia
Fatigue throughout the day
Labile emotions including irritability and spontaneous crying
Feelings of hopelessness and "doom and gloom"

The patient then started the treatment of the present invention, using 0.01 mg of the MAO-A activity stimulator (reserpine) per 0.05 ml cream, applied transdermally by rubbing the cream into the skin once a day in the morning. The patient experienced a headache that did not resolve spontaneously the first day, so the dose was reduced to 0.002 mg the second day. The headache resolved immediately with the lower dose of 0.002 mg and the patient reported alleviation of her symptoms of feeling hopelessness and "doom and gloom", but her other symptoms persisted. On the third day the dose was therefore increased to 0.004 mg of the MAO-A activity stimulator; in response, she reported improvement in her emotions stating, "I don't cry at the drop of a hat". At the 0.004 mg dose (reserpine) level her feeling of hopelessness was alleviated, and she was more emotionally stable as well, but she still experienced fatigue and insomnia. The does was consequently increased to 0.006 mg per day, at which point all of the patient's symptoms of depression were successfully alleviated. She has been on the treatment for eight consecutive months, using 0.006 mg per day of the reserpine applied transdermally, with no return of the symptoms of depression listed above.

It will be noted that in each of the examples the improvement or resolution of symptoms was essentially immediate, occurring within 1-4 hours of the first application of the treatment composition. This stands in dramatic contrast to the delay of 2-3 weeks characteristic of conventional treatments. Moreover, in all examples, the treatment has proceeded with no significant negative side effects; the preferred reserpine (and other rauwolfia alkaloids) have known negative side effects at higher dosage rates, however, the dosage rates used in the method of the present invention are well below those ranges. Moreover, the preferred MAO-A activity stimulator—reserpine—is comparatively economical, so that the invention can be practiced without prohibitive expense.

b. Autism Spectrum Disorder (ASD)

With respect to Autism Spectrum Disorder (ASD), the present invention is postulated on the belief that the increased serotonin and norepinephrine levels, increased HVA levels, the metabolic imbalances of elevated total cholesterol, elevated ACTH levels and low dihydroepiandosterone sulfate (DHEA-S) seen in ASD patients are similarly a result of deficient MAO-A activity, and that this decreased MAO-A activity results in the symptoms associated with ASD.

i. Theoretical Basis

As noted above, MAO-A is an enzyme expressed in the brain, that metabolizes histamine, serotonin, norepinephrine, and to a lesser extent dopamine. (Dopamine is predominantly metabolized by MAO-B). High levels of serotonin (hyperserotonemia) and high levels of norepinephrine are associated with ASD (Lake et al, 1977; Launay et al, 1988) Serotonin is a mediator of the hypothalamic-pituitary-adrenal (HPA) axis. Serotonin's regulation of the HPA axis is mediated via activation of the various serotonin receptors. The secretion of adrenocorticotropic hormone (ACTH) is mediated via the 5-HT1a, 5-HT2a, and 5-HT2c receptors. (Jergensen, 2007). Serotonin that has not been metabolized by MAO-A will be transported by the serotonin reuptake transporter to the 5-HT1a receptors (Larsson et al, 1990; Baumann & Waldmeier, 1984; Ma, 2008). This stimulation of the 5-HT1a receptor results in increased ACTH secretion that is seen in ASD (Curin, 2003).

Catechol-O-methyltransferase (COMT) can also stimulate ACTH secretion but this is dependent on low-expression MAO-A variant in the same individual (Jabbi et al, 2007).

ASD patients have a slowed response to stress despite elevated levels of ACTH (Marinovic', 2008). MAO-A knockout mice have demonstrated a diminished response to stress (Popova). Chronic stress in persons with MAO-A alleles associated with less transcriptional activity display a pattern of cortisol excretion—a decrease from overnight to daytime—that is suggestive of HPA axis blunting as compared to those persons with more active MAO-A alleles (Brummett et al, 2008). Children with infantile autism have shown an abnormal diurnal rhythm for cortisol production (Hoshino et al, 1987).

Increased levels of serotonin stimulates the release of hypothalamic corticotropin-releasing hormone (CRH), increases ACTH secretion 3-5 fold and increases secretion of proopiomelanocortin hormone (POMC) 15-27%, all of which have been shown to be elevated in ASD (Jergensen et al, 2002). POMC stimulates the production of Beta-endorphins, which has been shown to be high in many autistic patients especially those who display self-injurious behavior (Sandman et al, 2002).

DHEA-S is low in adult ASD patients (Strous et al, 2005). DHEA is synthesized in the zona reticularis of the adrenal cortex and MAO-A is widespread throughout the adrenal cortex and adrenal capsule (Dharia & Parker, 2004; Harper et al, 1999).

MAO-A is genetically expressed on the X chromosome, which may explain the hereditary prevalence of ASD. Two common alleles have been identified in humans, "low" and "high" transcriptional functionality. Therefore, males can be typed as either "low" or "high" types. High MAO-A activity genotype are less likely to develop antisocial problems. (Craig, 2005). Low activity alleles within the gene promoter region of the MAO-A gene were correlated in the autistic patients tested (Cohen et al, 2003; Davis et al, 2008). There was a consistent association between the "low activity" allele and larger brain volumes for regions of the cortex in children with autism. (Davis et al, 2008). Autistic infants have a smaller head circumference at birth and then undergo two phases of sudden excessive increase in head size between 1 to 2 months and 6 to 14 months. This increase in head size was related to greater cerebral cortex volume at 2 to 5 years of age (Courchesne et al, 2003). Individuals with the low activity allele MAO-A gene polymorphism display behaviors of alcoholism, antisocial personality, and impulsivity (Contini et al, 2006).

ASD patients such as those with Asperger Syndrome have elevated total cholesterol and low-density lipoprotein (LDL) levels (Dziobek et al, 2007). Higher total cholesterol, LDL/HDL ratios, and triglycerides were associated with low activity MAO-A alleles (Brummett et al, 2008).

A decrease in the MAO-A activity can decrease the mitochondrial complex II activity (reduced flavin adenine dinucleotide (FADH)) as it is dependent on the MAO-A activity (Heron et al, 2001). Inhibition of mitochondrial complex II results in an accumulation of dopamine's metabolite HVA (Cakala et al, 2006). HVA is elevated in ASD patients (Gillberg & Svennerholm, 1987).

Oxytocin is involved in the development of social and language communication skills. Deficient oxytocin innervation has been postulated as a potential contributor to the development of ASD. In a developmental hyperserotonemia model of autism in Sprague-Dawley rats, pregnant dams were administered a serotonin agonist. The dams' offspring displayed decreased bonding with the dam, increased gnawing reactions to novel stimulus, less behavioral inhibition, and had fewer olfactory-based social interactions. Post mortem analyses revealed a loss of oxytocin containing cells in the paraventricular nucleus of the hypothalamus in the pups that had been exposed to high levels of serotonin during gestation. (McNamara et al, 2008). Thus, the decrease in oxytocin associated with ASD may be in part due to high levels of serotonin.

ii. Method

The present invention provides a method for treatment of ASD by administration of a compound (which may be referred to for purposes hereof as an MAO-A agonist) that increases the catalytic activity of MAO-A in metabolizing serotonin and norepinephrine. Suitable compounds includes reserpine and reserpine analogues, as used herein, the term "reserpine analogue" refers to compounds having a pharmacological effect similar to reserpine, in effecting an increase in the catalytic activity of MAO-A. Reserpine in particular has been shown to activate MAO-A (Youdim & Sandler, 1968; Vijayalakshmi et al, 1978). It is anticipated that other rauwolfia alkaloids and their analogues may also be useful.

The treatment composition of the present invention may be administered by any suitable means, such as orally, or by transdermal application, or injection, or inhaler, to give just a few examples. However, administration by transdermal application is generally preferred, in that this provides significant advantages in terms of ease of use and more consistent dosage levels.

Accordingly, a preferred composition for use in the treatment of ASD is formed by the preferred MAO-A agonist reserpine in a transdermal disc or spray. When transdermally administered, daily dosage is significantly less than 0.03 mg/day and preferably within the range of about 0.002-0.02 mg/day, with a range of about 0.005-0.01 mg/day being most preferred. The treatment composition is suitably applied in a single daily dose, e.g., 0.01 mg of the MAO-A agonist in 0.05 ml of spray solution applied once every morning.

The present invention is based on the inventor's hypothesis that the cause of many of the symptoms of ASD is related to elevated levels of serotonin. This is distinct from previous treatments, such as, antidepressants that have been used to relieve some of the symptoms of ASD. Antidepressants such as Selective Serotonin Reuptake Inhibitors are aimed at increasing the levels of serotonin whereas the present invention is aimed at decreasing the levels of serotonin. The use of a MAO-A agonist therefore runs directly contrary to the purpose of SSRI antidepressants that have been administered "off-label" to treat the symptoms of ASD.

iii EXAMPLES

The following illustrative examples relate to actual practice of the invention described above, and its success in alleviating the symptoms of ASD.

Example One

Improvement of Symptoms Following Administration of the Present Invention (Transdermal Reserpine) in a 14 Year-Old Boy with Autism Case Presentation The patient is a 14 year-old male diagnosed with mild Autism at the age of 3 years 11 months. He is the older of two children and lives with his mother and father. The patient was referred through community resources. His parents were seeking assistance in managing specific symptoms of stereotypical behavior; impaired social interactions and extended periods of irritability typified by screaming, crying and inconsolability.

Due to a history of multiple failed attempts at treating this patient's symptoms with typical psychopharmacologic agents, he was administered a trial of transdermal Reserpine. After three weeks of this treatment, the patient demonstrated significant improvements in his social interactions, language, and attention. His mood improved, and he exhibited a markedly decreased amount of anxiety. There was a significant change in his quantitative Electroencephalogram noted after three weeks of treatment (FIG. 5).

Medical and Psychiatric History

The patient's mother reports an uncomplicated pregnancy. Labor was induced, and the patient's mother received an epidural during labor. The patient was 8 lbs, 4 ounces at birth. His APGAR scores were normal, and he enjoyed excellent health as a newborn. The patient had multiple ear infections after one year of age, and incurred an atypical reaction to antibiotics with decreased Neutrophils and Platelets around 14 months of age. He received a bone biopsy at that time. The patient has had significant reflux beginning at age 6 and continuing to the present day. This is managed with daily Prilosec. The patient also takes Singular for mild asthma. The patient's reflux has exacerbated his mood and behavior problems. The patient has no vision or hearing abnormalities. There is no history of surgery, or hospital admission.

The patient has been managed on various psychiatric medications with no significant benefit. At the age of 6 the patient began having frequent meltdowns, and would become overwhelmed due to over stimulation. This would cause him to pull at the corners of his eyes and cover his ears. He was placed on Prozac at the age of 6 to help with these episodes and remained on this medication for approximately 3 years. His parents discontinued this medication due to concerns over long-term toxicity and he was not treated with any psychoactive medications until the age of 12. At this point, he began having more frequent, prolonged and intense behavioral decompensation. It became difficult to go out in public with the patient, as he became prone to crying and screaming episodes triggered by seemingly insignificant events.

During the ensuing 2 years, the patient has had trials of several medications at therapeutic doses for adequate time-periods. In chronological order, the following medications have been administered: Risperidone, S-Citalopram, Buproprion, Methylphenidate, Amphetamine Salts, and quetiapine. Only the latter has shown any functional improvements, and has been continued on an as needed basis by the patient's parents.

Prior to treatment with the present invention, the patient's current regimen includes methyl-B12 injection, Vitamin C 100 Mg, Magnesium 250 Mg, quetiapine 25 mg PRN agitation, and Hyperbaric Oxygen Therapy.

Developmental History

The patient was sitting at 6 months, crawling at 9 months, and walking at 15-16 months. He rode a tricycle at 3 and ½ and a bicycle at 6 and ½. According to the patient's parents he has difficulty with fine motor coordination. In terms of language development, the patient had a vocabulary of 3 to 4 words at 12 months of age, 2 word combinations began at age 2. During early childhood, the patient exhibited early and delayed echolalia. He would get fixated on certain books and movies, and remains fixated over a very small selection of movies and books that have not changed since childhood. He will also ask the same questions repeatedly, despite knowing the answers already. The patient frequently ruminates over a very narrow range of stories that occurred many years in the past.

Social History

He is socially motivated, but exhibits poor social skills. Although, generally accepted by peers, the patient is not sought after to spend time with individuals outside of school. He can occasionally exhibit mild aggression toward his younger brother and mother, and will exhibit remorse after such events.

School History

The patient attends middle school. At school, the patient does not typically present any behavior problems. He requires an Individualized Education Plan and occasionally becomes frustrated with more difficult academic work. He reports that he likes science, math and spelling. His least favorite subject is writing. The patient does well with routine tasks and can become anxious when his routine changes. He participates in Basketball and Tennis.

Family History

The patient's mother has a bachelor's degree and is a stay at home mother. His father also has a Bachelor's degree, is completing his Master's degree and works as the director of development at a non-profit children's clinic. The patient's brother is developmentally normal. There is no family history of Pervasive Developmental Disorders. The patient's maternal uncle exhibits symptoms consistent with Attention Deficit Disorder, and learning disability.

Mental Status Exam

The patient has dark hair, and brown eyes. He is tall and lean for his age. He lacks typical facial reactivity. Generally, he is cooperative, but can become fixated on time. He repeats phrases like, "Five minutes until we're done, how long until this is finished?" Eye contact is variable. At times the patient can become uncooperative. Self-stimulatory behavior is exhibited through hair pulling, covering the corners of his eyes, and ears, and hyperkinetic movements.

The patient speaks in a high-pitched, sing-song voice. Articulation is clear. Speech is remarkable for unusual prosody. Volume and rate are variable, with notable changes between loud and soft, rapid and slow. Emphasis is unusual. Echolalia is present.

Affect is euthymic, with significantly increased reactivity if provoked with questions about making choices. Range is elevated, and can become dysphoric or irritable easily.

Thought process is non-linear. The patient will begin asking about unrelated events, or blurt out non-sequtiors and platitudes, such as "you're not a shot doctor," at random. Thought content does not match situation and is dependant on the particular topic the patient is fixated on that day. These topics are of narrow range and often occurred in the remote past. The patient tends to interpret questions in an overly literal manner. If asked to look over a picture, we will gaze off in the distance.

Insight is poor. The patient does not have awareness that he has any difficulties. He will become boastful when he knows he is maneuvering a social situation correctly. For example, when he meets an unfamiliar individual, and asks them their name, he will then announce that he accomplished this task.

Judgment is immature. The patient does not complete age appropriate tasks, and requires assistance in day-to-day activities of daily living. He is unable to manage money, or make simple choices regarding what he would like to eat. He is unable to prepare food for himself.

Physical Exam

Physical exam reveals a young male with no physical abnormalities. Vision and hearing are normal. Gross examination of neurological, cardiovascular, respiratory and gastrointestinal system are normal.

Psychological Assessment

The patient was first evaluated at 3 years 11 months, again at 6 years 8 months, 9 years 8 months, and 11 years 2 months. He has intellectual and academic abilities which range widely between borderline and high average. Each evaluation documented and supported the diagnosis of Autism.

The patient has average skills in reading. Relative weaknesses are observed in visual-motor skills, fine motor skills, application, reasoning skills, and comprehension. He has strengths in non-language problem solving skills.

The patient obtained a Full Scale IQ of 70 on his most recent psychological testing with the Wechsler Intelligence Scale for Children (WISC-IV). Subtest scores are as follows

| Verbal Comprehension Subtests | |
| --- | --- |
| Similarities | 5 |
| Vocabulary | 1 |
| Comprehension | 1 |

| Perceptual Reasoning Subtests | |
|---|---|
| Block Design | 9 |
| Picture Concepts | 5 |
| Matrix Reasoning | 9 |

| Working Memory Subtests | |
|---|---|
| Digit Span | 10 |
| Letter-Number Sequencing | 1 |

| Processing Speed Subtests | |
|---|---|
| Coding | 9 |
| Symbol Search | 8 |

On the Vineland Adaptive Behavior Scale (Vineland-II) the patient had the following scores.

| Domain | Standard Scale | Percentile | Adaptive Level |
|---|---|---|---|
| Communication | 70 +/- 8 | 2 | Low |
| Daily Living | 68 +/- 8 | 2 | Low |
| Socialization | 68 +/- 8 | 2 | Low |
| Adaptive Behavior Composite | 67 +/- 6 | 2 | Low |

On the Child Behavior Checklist (CBCL) the patient had significant elevations on the attention problems, withdrawal/depression, and thought problems scales. His scores were consistent between his parents' and commensurate with a diagnosis of Autism.

Diagnosis and Treatment

Based on history, physical examination, clinical observation, and psychological testing, the patient meets criteria for the diagnosis of Autism, and Borderline Intellectual Functioning based on the World Health Organization (W. H. O.) International Classification of Diseases (ICD-10).

Identified problems in the patient were communication impairment, poor social interaction, problem solving difficulties, and behavioral problems characterized by unwarranted screaming, affective disturbance, social isolation, hyperactivity, and anxiety.

The patient's treatment includes a multi-disciplinary approach using behavioral, educational, nutritional, and pharmacological interventions.

Prior to the present invention treatment of transdermal reserpine, the patient's treatment regimen included:
Transdermal B-12
Super-Nu Thera Multi Vitamin
Omega 3 Fatty Acids
Vitamin C
Zinc
Magnesium
quetiapine 12.5 mg as needed for agitation He has completed 60 Neurofeedback treatments, and was participating in Hyperbaric Oxygen Therapy during the course of his administration of the present invention.

Prior to administration of the present invention (transdermal reserpine), the patient's parents were provided with an informed consent documenting the potential risks, benefits and alternatives to this treatment. The patient was started on a dose of Reserpine at a 4× dilution resulting in a total dose of 0.01 mg. This resulted in some increased hyperactivity, and the dose was reduced to 0.005 mg. He was also given approximately 1400 mg of Calcium every morning. It is necessary to co-administer Calcium due to an increase in the amount of calcium excreted in the urine as a result of reserpine administration.

After 3 weeks of treatment at the reduced dose, the patient started using several meaningful sentences in succession, carrying on appropriate conversations, became more tuned in and interested in other people, exhibited less repetitive behaviors. During the course of present invention treatment, the patient had no temper outbursts resulting in no quetiapine administration. There was a mild increase in motor hyperactivity.

Quantitative Electroencephalogram qEEG is a noninvasive instrument, capable of assessing the resting and evoked activity of the brain with sensitivity and resolution superior to those of any other method. In a paper by Thatcher et al, an Autistic signature was reported. This electrical signature is typified by high amounts of low and high frequency waves and low amounts of mid-range electrical activity. The spectral analysis of this signature has the shape of a parabola, or U-shape. This shape can be seen in first spectral analysis listed in FIG. 5. The first three scans represented on the color brain maps of this patient exemplify the signature mentioned above. The fourth and final scan does not show this U-shaped curve.

The patient has had serial Quantitative Electroencephalograms (qEEG), during the course of his treatment. Analysis was conducted using Neuroguide 2.5, a widely accepted and statistically valid instrument (Thatcher et al, 2003). Significant changes were noted after administration of the present invention treatment, as seen in FIG. 6, which shows qEEG before starting HBOT, qEEG after 13 sessions of HBOT, qEEG after 25 sessions of HBOT, and qEEG after 35 HBOT sessions and 3 weeks after beginning Respen treatment.

Hyperbaric Oxygen Therapy

This is a widely accepted treatment used to manage a range of disorders. Hyperbaric Oxygen Therapy (HBOT) has been shown to provide benefit in Autism (Rossignol et al, 2007). This therapy is administered in a sealed chamber at a pressure equal to 1.4 ATM and an oxygen concentration of 24%. A typical course of treatment consists of 40 sessions lasting 60 minutes in duration. This patient suffered some behavioral dyscontrol during his HBOT treatments. This has previously been recorded as a side effect of HBOT treatment in Autism. The behavioral dyscontrol is consistent with the patients qEEG showing an increase in High Beta activity after starting HBOT. The High Beta activity appears to subside after starting the present invention (transdermal reserpine).

Example Two

Improvement of Symptoms Following Administration of the Present Invention (Transdermal Reserpine) in a 5 Year-Old boy with Autism Case Presentation The patient is a 5-year old male diagnosed with Autism at age 4, but had displayed symptoms associated with ASD since 2 years of age. The symptoms included tantrums in which the child would throw himself to the floor or around the room screaming and crying and these tantrums would last 1½-3 hours in duration. These outbursts were spontaneous or could be triggered by a nominal stimulus such as being asked to perform a task such as to close a door. The child also would not initiate or mimic any affectionate behavior to his father or mother such as a hug or kiss. He had a very short attention span and he was extremely hyperactive. By age 4 the child was displaying selective mute behavior in which he would not speak to his grandparents, friends of the family or strangers. He would not speak to peers or teachers at pre-school and did not engage in play with the other children.

After his diagnosis of autism at age 4, he was started on a gluten free diet. After a few months on the gluten free diet, he started to talk with neighbors and family but only on a very limited basis. He still refused to speak at pre-school or at church. He also would still not engage in play with other children at pre-school, and only for very brief moments with his younger brother.

Soon after turning 5 years of age, he began receiving transdermal reserpine 0.01 mg per day. He immediately exhibited an increase attention span and could easily stay focused on a task for 30 minutes or more. He began engaging in play with his sibling and they would play together for several hours. He become more affectionate toward his parents and grandparents and would initiate a hug or kiss as well as return such affection when he was given a hug or kiss. He began engaging in meaningful conversation with his sibling and parents and grandparents. Prior on just the gluten free diet, many of his words were incomprehensible and nonsensical. After starting the transdermal reserpine of 0.01 mg per day he remained focused in a meaningful conversation with his parents and sibling and all of his speech is clear and comprehensible.

After 2 months on the transdermal reserpine, a trial of taking him off of the gluten free diet and continuing on the transdermal reserpine at 0.01 mg per day was initiated. He displayed some moments of hyperactivity periodically so his dose of trasndermal reserpine was increased to 0.015 mg per day but this resulted in him becoming very hyperactive and aggressive. His dose of reserpine was decreased back to 0.01 mg per day and he has maintained his improvements in speech, social behavior, and attention span. He will still have some periods of hyperactivity if he eats very much gluten containing foods.

Example Three

Improvement of Symptoms Following Administration of the Present Invention (Transdermal Reserpine) in a 12 Year-Old Male with Autism Case Presentation The patient is a 12-year old male who was diagnosed with Autism at 3 years of age. The patient appeared to be a normal little boy until age 2. His mother reports that she would frequently sit and read him books and he was beginning to pronounce some words, such as "truck", "mama", "dada", and "duck". He would point at things when his mother would ask him to show her where an object was which was evidence that he was comprehending language. Then one day his ability to understand and mimic speech disappeared. His mother said that she was reading him a book and he grabbed the book and tore it up and from that day forward, he refused to be read to or have any interest in books. He lost the first words he had mastered and has been nonverbal since with the exception of making the "aaaaaaaaa" sound as he bangs two plastic sticks together repeatedly for hours on end. His mother refers to this as "stimming". He has never received any vaccinations.

He displays other severe symptoms of autism such as he is oblivious to others in his environment and doesn't explore things in his environment such as toys, open drawers or cupboards to explore what they contain. He will occasionally make eye contact, he engages in constant repetitive movement such as jumping on a small trampoline, banging plastic sticks together, and/or rocking back and forth when sitting in a chair. He won't drink from a cup or use eating utensils. He will only eat pureed food except for one type of cracker. He requires constant supervision as he likes to eat paper. He has eaten magazines, books, even dollar bills. He requires constant 1-on-1 supervision to remain clothed at school or home. If he is left unattended for just a few minutes, he will disrobe to complete nakedness and he appears to be unaware that others around him are clothed. He displays limited affection and rejects being touched or hugged. He often grabs his head and screams as if in severe pain such as a headache. He doesn't engage in play with his younger brother or children at school. He suffers from insomnia and requires sleeping medication to be administered at least twice throughout the night and many nights the sleeping aid is ineffective. He is toilet trained but on several occasion has defecated in the sink and tried to push the feces down the drain with his hands.

He attends public school with an aide but is unable to perform any schoolwork activities even of a preschool level. He can't trace a shape such as a circle as he doesn't appear to comprehend the task and his fine motor skills are not highly developed. His gross motor skills are very good. His teachers at school have been trying to teach him to use a "talk box" to express his wants but he has been unsuccessful in accomplishing this.

Numerous treatments have been tried with none to minimal success i.e. hyperbaric oxygen, gluten free diet, chelation therapy for heavy metals, vitamin therapies, depakote, Seroquel, Adderal, Ritalin, melatonin, naltrexone, antidepressants. A low dose of two selective serotonin reuptake inhibitors have had a minimal effect in decreasing his physical outbursts that have resulted in injury such as throwing himself through a sliding glass door.

The patient began transdermal reserpine 0.01 mg per day and immediately his "stimming" (banging of the plastic sticks) was reduced to only infrequent occurrence. By the second day of transdermal reserpine administration, he left his clothes on without supervision and he could sit quietly. Within the first 30 days of initiating reserpine 0.01 mg per day he started making some new speech sounds, i.e consonant sounds, k, d, m, b. In the second month of treatment with transdermal reserpine, the patient attempted to say a four word sentence as heard by his father and mother. He distinctly said two incomprehensible words followed by "daddy" followed by another garbled word. After 2 months of transdermal reserpine 0.01 mg, he was at school and his aide was trying to get him to indicate what he wanted on the "talk box". The patient became frustrated and shouted out very clearly the words, "I'm hungry".

The patient's parents report that since being on the transdermal reserpine 0.01 mg per day, he will now look at them and smile when spoken to and appears to understand language better, he will wrestle with his father in play, he will seek out his brother and play with him, he on occasion has curled up next to his mother on the couch wanting to be close to her and will allow her to hug him and he has even initiated the hug. He now follows directions such as when his mother asked him to wash his hands, and another time to get off of the bleachers and go walk around the track at his school while she was talking to his teacher. He has started exploring his environment in that he opened a drawer to look inside it, and he was found turning the dimmer switch on the wall and was watching and correlating that he could make the light go dimmer and brighter as he turned the switch. His brother is taking piano lessons, and the patient now goes over to the piano and quietly plays the piano trying to mimic what his brother's playing.

He continues on the transdermal reserpine at 0.01 mg per day without any side effects and continues to make subtle slow improvements in social behavior, speech, attention span, and awareness and interaction with his environment.

iii. Homeopathic Dosages

As part of the present invention, it has been found that with at least some individuals effective treatment of ASD may be achieved using dosages in the ranges below those discussed above, in particular reserpine attenuated to homeopathic ranges. As a non-binding hypothesis, it is believed that the reduced concentrations of reserpine may result in reduced metabolites of the compound, that in higher concentrations may in at least some instances impair the ability of cellular storage vesicles to uptake and store serotonin, rather than reserpine itself as has been postulated in some literature.

For treatment of ASD using reserpine in homeopathic amounts, effective results were observed utilizing transdermal administration of reserpine at a dilution of 12 C, on the standard homeopathic "C" dilution scale, administered at least once per day. Based on these results, it is envisioned that effective treatments may also be achieved using lesser or greater dilutions, particularly at dilutions less than 12 C (e.g., in the dosages of 12 C-1C). It has furthermore been discovered that use of reserpine at homeopathic dosages enhances stability and shelf life and simplifies storage, as compared with compositions employing reserpine in higher concentrations. The homeopathic reserpine compositions may also be administered topically as well as transdermally.

The following illustrative examples relate to actual practice of the invention, using transdermal administration techniques substantially as described above, but with reserpine at a 12 C homeopathic dilution.

Example One

Improvement of Symptoms Following Transdermal Administration of 12c Reserpine in a 8 Year Old Male with Autism.
Case Presentation The patient is an 8 year old male diagnosed with Autism. Substantial improvements were reported following treatment as described in the preceding sections, utilizing reserpine, administered at a rate of 0.01 mg/day. Additional gains were observed, however, following a subsequent shift to administration of the attenuated reserpine in homeopathic dosages.
Method A 12 C dilution of reserpine was prepared using conventional homeopathic dilution techniques known to those skilled in the relevant art. Transdermal patches, as described above, were then prepared containing the 12 C reserpine and sealed in foil. The prior treatment employing the reserpine dosage of 0.01 mg/day was terminated. The treatment then commenced with daily administration of the 12 C reserpine composition, with additional performance and psychological gains as set forth below.
Observed Improvements The following improvements were observed, developing over a period of approximately one month after commencing daily administration of the 12 C reserpine composition.

First, a pronounced improvement in patience was noted. The patient began playing with his toys for extended periods of time, whereas prior he would only play for a few minutes and then lose interest; he also began asking others to join him in play, which was a new development. Treatment with the 12 C reserpine commenced prior to the holiday season, which afforded an opportunity to compare the patient's behavior with that during prior birthdays, holidays and similar high-intensity events: In contrast to similar occasions previously, the patient was observed to patiently open presents, and also carry on meaningful conversations with others, to the extent of initiating conversation by asking questions, despite several people being present in the room. This was a distinct contrast with the past, where similar events had presented too much commotion for the patient to cope with.

The patient was also observed to demonstrate increased patience and concentration on a daily basis. He demonstrated an increased willingness to listen and answer questions, and to ask questions in turn. Overall, his demeanor was more quiet and calm than before. As one example, the child's patience improved to the point that he was able to sit still through the entire time of a haircut, something of which he had not previously been capable.

Also, subsequent to commencing treatment with the homeopathic reserpine, the patient's teachers reported a pronounced improvement in academic performance, as well as increased concentration and patience. The teachers also reported an improved level of interaction between the patient and his schoolmates. Notable examples included carefully passing out papers in the classroom and patiently waiting in line to play jump rope and other games at recess; an increased willingness to wait his turn was also noted when playing cards and other games at home. Overall, the patient exhibited a much improved interest in academic subjects, coupled with an increased willingness to ask questions and otherwise engage in the educational environment.

More generally, the patient's overall behavior and demeanor improved substantially over the month following commencement of the daily 12 C reserpine treatment. His parents reported a more positive, happy attitude, combined with more meaningful discussions and questions, in contrast with previous louder, more disruptive behavior. He exhibited an increasing willingness to engage in household activities and help with and complete chores requiring a degree of concentration, including folding clothes, washing dishes, and washing counters. Similarly, he exhibited significantly improved attention and social engagement at mealtimes, for example reminding his father that it was time for breakfast and offering to refill other's glasses when he observed them to be empty, as well as a marked improvement in simply being able to remain calm and engage in a meaningful conversation throughout the meal. The patient's parents further reported a pronounced improvement in the patient's vocabulary and sentence length and structure during the relevant period.

At one point the patient missed his treatment for three days, during which his parents and teachers noticed a decline in attitude and performance, including an incident in which he threw his calendar outside in the snow. Treatment with the 12 C reserpine was restarted and improvement in the patient's condition resumed.

Example Two

Improvement of Symptoms Following Transdermal Administration of 12 C Reserpine in an Adolescent Male with Autism
Case Presentation The patient is a 14 year old male diagnosed with autism. He has exhibited symptoms characteristic of ASD including agitation, pronounced lack of patience, obsessive/repetitive behaviors, and difficulty engaging with others in his environment. These symptoms have been coupled with a pronounced lack of emotional development, poor social skills, and an inability to perform basic tasks including attending to personal hygiene.

The patient had previously been treated with reserpine at a dosage of 0.01 mg/day, as described above, with substantial improvement. However, subsequent treatment with 12 C reserpine administered transdermally was observed to lead to additional improvements, as are described below.

Method

A 12 C dilution of reserpine was prepared using conventional homeopathic dilution techniques. Transdermal patches were prepared containing the 12 C reserpine, the patches then being sealed in foil for transportation/storage prior to use. The previous treatment utilizing reserpine at a dosage of 0.01 mg/day was terminated. Treatment then commenced with daily administration of the 12 C reserpine transdermal patches.

Observed Improvements

The following improvements were observed after commencing daily administration of the 12 C reserpine composition.

As reported by the parents, the patient demonstrated an increased ability to focus and exercise patience, as compared with prior levels. The patient's interaction with his younger brother improved markedly, with much improved ability to be kind and patient with his sibling.

The parents reported that the improvements in focus and patience were particularly notable in the context of family projects and tasks that had previously been highly challenging. For example, a routine family task involves cutting and hauling wood, during which the patient had to be prompted repeatedly—e.g., "get a log," "get a log," "get another log" and so on—and had previously led to the development of major tantrums. After commencing the daily 12 C reserpine treatment, the patient improved and was able to maintain focus during such projects, for example, bringing logs and so forth without requiring constant direction. Moreover, his parents were able to redirect his tasks without a major upset. The patient also showed greater enjoyment and energy when carrying out the tasks.

The improvements in focus and patience were accompanied by a pronounced decrease in anxiety. The patient had a previous pattern of verbalizing repeatedly a feeling that he was in trouble, which resolved following commencement of the 12 C reserpine treatment. He was also observed to be less readily distressed when he felt he had been left alone, without it having actually occurred, and was more easily calmed when he did become distressed.

The parents also reported a decreased tendency for the patient to obsess on certain activities/interests, and an improved ability to be redirected without becoming angered or upset.

The patient also demonstrated improved focus in performing the basic tasks of personal hygiene; for example, the patient was able to shower and wash himself properly without repeated prompts from his parents, whereas he previously had been unable to do so. His emotional behavior also improved markedly, from an excessively dependent and infant-like condition exhibited previously.

The patient demonstrated corresponding improvements in his educational environment, with the observations that he had a much better focus on school work and that his increased patience and willingness to be redirected made him much more receptive to teaching.

c. Schizophrenia i. Hypothesis

A deficiency in MAO-A activity can result in mitochondria complex I dysfunction. A decrease in the MAO-A:MAO-B ratio results in a decrease in the mitochondria complex I activity (NADH dehydrogenase) and alpha-ketoglutarate dehydrogenase (KGDH) which impedes ATP production (Gluck & Zeevalk, 2004; Bai et al, 2005). Furthermore, like depression and depressive disorders, the cerebral spinal fluid (CSF) levels of the serotonin metabolite, 5-HIAA, from the deamination of serotonin by MAO-A are significantly lower in schizophrenia (Gattaz et al, 1982). Thus, the current invention is based on the non-binding hypothesis that schizophrenia patients have decreased norepinephrine and serotonin metabolism due to inadequate MAO-A activity.

The etiology of the hypothesized decreased MAO-A activity is likely multifaceted: genetic, environmental, toxins, stress, and lipid peroxidation. One of the contributing factors may be iron deficiency, either due to an absorption problem, insufficient intake, or decreased transferrin production. Iron deficiency can decrease MAO-A activity resulting in increased levels of norepinephrine and serotonin (Hu et al, 1996). Iron deficiency has been associated with schizophrenia and autism (Dosman et al, 2007; Kuloglu et al, 2003; Insel et al, 2008). Iron supplementation has resulted in some improvement in sleep in autistic patients and a 27% decrease in the rate of schizophrenic spectrum disorders in the offspring for every 1 Gram/dl mean maternal hemoglobin concentration (Dosman et al, 2007; Insel et al, 2008).

Reserpine is an MAO-A agonist, meaning it stimulates the activity of MAO-A (Vijayalakshmi V. et al, 1978). Reserpine has been used in schizophrenia prior to the current invention but all of the known literature teaches that the use of much higher doses of reserpine are needed, and none of the known literature teaches the use of the transdermal administration of reserpine that the current invention employs. Moore and Martin (1957) studied the use of oral and intramuscular (IM) injections in schizophrenic patients; Moore and Martin followed the dosing guidelines of Kline (1955) which were 3 mg orally daily throughout the treatment period in conjunction with 5 mg IM on the first evening, and 10 mg IM nightly for 3-7 weeks, reducing this to 5 mg IM on alternate nights for two weeks and finally 2.5 mg on alternate nights before discontinuing the injections (Moore and Martin, 1957).

In a study by Shepherd and Watt (1956) comparing chlorpromazine to reserpine in schizophrenia, doses of reserpine utilized were 10-15 mg per day orally. Due to an administrative error, the reserpine dose was reduced to 0.75 mg per day for Group A in the first period of the study and "this quantity of reserpine was regarded as resembling more an inert substance than the drug in the treatment of such severely ill patients and it was thought advisable to include chlorpromazine and reserpine in full dosage in the remaining periods" (Shepherd and Watt, 1956, page 233).

Reserpine has been used to treat agitation in schizophrenic patients dosage ranges of 0.1-1.0 mg with the usual starting dose of 0.5 mg orally per day. (http://www.drugs.com/pro/reserpine.html). Currently reserpine is no longer recommended or recognized in the treatment of schizophrenia perhaps due to limited if any efficacy seen at these lower ranges as reported in Shepherd and Watt and the increased risk of the development of depression associated with the use of reserpine. (http://www.inchem.org/documents/pims/pharm/reserpn.htm#SectionTitle:4.1%20%20Indications).

The dosage range employed in the method of the invention for treating the symptoms of schizophrenia is about 0.002-0.02 mg per day, preferably between about 0.005-0.01 mg per day, with the preferred dose generally being about 0.01 mg per day via a transdermal, solution in a metered spray device. These dosage ranges are 10-7,500 times less than the dosage ranges described in the above literature. Furthermore, Shepherd and Watt teach that reserpine in a dose of 0.75 mg per day resembled an inert substance, and that doses of 10-15 mg per day orally were needed to effectively treat schizophrenia.

ii. EXAMPLES

Example One

A 40-year-old male, 6 ft., 180 lbs., diagnosed with chronic schizophrenia when he was 32 years of age. His symptoms were anxiety, inability to concentrate and focus, frequent inability to complete a task, poor memory, delusions, and conversational responses not consistent with topic being discussed.

The patient had a history of being treated with Zyprexa (antipsychotic) and Depakote (anticonvulsant). These medications caused him to be extremely lethargic and obese so they were discontinued and he was started on Abilify (antipsychotic) which he tolerated better but still had many symptoms unresolved. The patient reported his dislike of taking a pill and required daily supervision to insure that he swallowed the pill.

He stopped the Abilify the day before he started the treatment of the present invention, of transdermal reserpine via a metered sprayer. He applied the reserpine spray to his forearm and reported feeling severely depressed within 30 seconds of rubbing the spray into his skin. He also complained of rapid heart rate, and anxiety. All of these symptoms resolved within 2-3 hours of applying the reserpine spray to the skin and his sister whom he lives with reported that he was more focused, he had clearer thoughts and carried on conversation and remained engaged in the topic being discussed. His sister described him as "completely normal". The symptoms of severe depression, anxiety and rapid heart rate returned the next 2 days upon applying a dose of the reserpine spray transdermally but they were slightly less severe and they resolved within 2 hours of applying the dose. On the fourth day of applying the reserpine transdermal spray, none of these side effect symptoms occurred and his sister said that he completed a list of chores that she gave him without supervision and the need to be reminded to stay on task. He was even able to go to the store and pick up a list of things and cook dinner that evening. On the fifth and sixth day he took the initiative to apply the sprays himself without supervision and remarked that he liked not having to take a pill. On the sixth day he became very aggressive and his sister discovered that he had not taken the required calcium of 2,000 mg with breakfast. Upon learning of this, his sister directed him to take the calcium and within one hour he was calm and happy.

It has been found important that a patient take additional calcium daily, typically 2,000 mg of calcium at breakfast, when using reserpine or an MAO-A agonist in accordance with the present invention. Without this precaution reserpine or an MAO-A agonist can cause hypocalcemia, low blood calcium.

It is believed that the side effects that this patient experienced were due to the Abilify that was still in his system. Abilify is a partial 5-HT1A agonist, which decreases the amount of serotonin that is released into the nerve synapses. The residual Abilify in his system was decreasing the level of serotonin in the synapses and the reserpine through its activation of the MAO-A activity rapidly depleted the available serotonin. Once the residual Abilify was cleared from his system the side effects resolved.

It is to be recognized that various alterations, modifications, and/or additions may be introduced into the construction and arrangements of parts described above without departing from the spirit or ambit of the present invention as defined by the appended claims.

CITED REFERENCES 1. http://www.cdc.giv/ncddd/autism/faq_prevalence.htm
2. Launay JM, Ferrari P, Haimart M, Bursztejn C, Tabuteau F, Braconnier A, Pasques-Bondoux D, Luong C, & Dreux C. (1988). Serotonin metabolism and other biochemical parameters in infantile autism. A controlled study of 22 autistic children. *Neuropsychobiology* 20(1), pp. 1-11.
3. Lake CR, Ziegler MG, & Mruphy DL. (1977, May). Increased norepinephrine levels and decreased dopamine-beta-hydroxylase activity in primary autism. *Arch Gen Psychiatry* 34(5), pp. 553-556.
4. Hranilovic D, Bujas-Petkovic Z, Vragovic R. Vuk T, Hock K, & Jernej B. (2007, November). Hyperserotonemia in adults with autistic disorder. *J. Autism Dev Disord* 37(10), pp. 1934-1940.
5. Gillberg C & Svennerholm L. (1987, July). CSF monoamines in autistic syndromes and other pervasive developmental disorders of early childhood. *Br J Psychiatry* 151, pp. 89-94.
6. http://autism.about.com/od/treatmentoptions/p/drugtreatments.htm
7. Jergensen HS. (2007, November). Studies on the neuroendocrine role of serotonin. *Dan Med Bull* 54(4), pp. 266-288.
8. Ma Z, Zhang G, Jenney C. Krishnamoorthy S, & Tao R. (2008, July 7). Characterication of serotonin-toxicity syndrome (toxidrome) elicited by 5-hydroxy-1-trytophan in clorgyline-pretreated rats. *Eur J Pharmacology* 588(2-3), pp. 198-206.
9. Larsson LG, Renyi L, Ross SB, Svensson B, Angeby-Moller K. (1990, February) Different effect on the responses of functions pre- and postsynaptic 5-HT1A receptors by repeated treatment of rats with the 5-HT1A receptor agonist 8-OH-DPAT. *Neuropharmacology*, 29(2), pp. 86-91.
10. Baumann PA & Waldmeier PC, (1984, January). Negative feedback control of serotonin release in vivo: comparison of 5-hydroxyindolacetic acid levels measured by voltammetry in conscious rates and by biochemical techniques. *Neuroscience,* 11(1), pp. 195-204.
11. Jabbi, M, Korf, J, Kema, IP, Hartman C, van der Pompe, G, Minderaa, RB, Ormel, J & den Boer, JA. (2007, May). Convergent genetic modulation of the endocrine stress response involves polymorphic variations of 5-HTT, COMT and MAOA. *Mol Psychiatry,* 12(5), pp. 483-490.
12. Curin JM, Terzic, IM, Petkovic, zB, Zekan L, Terzic, IM, & Susnjara IM. (2003, August). Lower cortisol and higher ACTH levels in individuals with autism. *J Autism Dev Disord* (33(4), pp. 443-448.
13. Marinovic-Curin J, Marinovic-Terzic I, Buj as Petkovic Z, Zekan L, Skrabic V, Dogas Z, & Terzic J. (2008, February). Slower cortisol response during ACTH stimulation test in autistic children. *Eur Child Adosc Psychiatry* 17(1), pp. 39-43.
14. Popva NK, Masiova LN, Morosova EA, Bulygina VV, & Seif I. (2006, February). MAO-A knockout attenuates adrenocortical response to various kinds of stress. *Psychoneuroendocrinology* 31(2), pp. 179-186.
15. Brummett BH, Boyle SH, Siegler IC, Kuhn CM, Surwit RS, Garrett ME, Collins A, Ashley-Koch A, & Williams RB. (2008, October). HPA axis function in male caregivers: effect of the monoamine oxidase-A gene promoter (MAOA-uVNTR). *Biol psychol* 79(2), pp. 250-255.

16. Hoshino Y, Yokoyama F, Watanabe M. Murata S, Kaneko M. Y Kumashiro H (1987, June). The diurnal variation and response to dexamethasone suppression test of saliva cortisol level in autistic children. *Jpn J Psychiatry Neurol* 41(2), pp. 227-235.
17. Jergensen H, Knigge U, Kjaer A, Moller M, & Warberg J. (2002, October). Serotonergic stimulation of corticotrophin-releasing hormone and proopiomelanocortin gene expression *J Neuroendocrinology* 14(10) pp. 788-795.
18. Sandman CA, Touchette P, Maron S, Lenjavi M, & Chicz-Demet A. (2002 Oct. 15). Disregulation of proopiomelanocortin and contagious maladaptive behavior. *Regul Pept* 108(2-3), pp. 179-185.
19. Strous RD, Golubchik P, Maayan R, Mozes T, Tuati-Werner D, Weizman A, & Spivak B. (2005, May). Lowered DHEA-S plasma levels in adult individuals with autistic disorder. *Eur Neuropsychopharmacology* 15(3), pp. 305-309.
20. Dharia, S, & Parker, CR Jr. (2004, November). Adrenal androgens and aging. *Seminar on Reproduction Medicine*, 22(4), pp. 361-8.
21. Haroper, AJ, Buster, JE, & Casson, PR (1999). Changes in adrenocortical function with aging and therapeutic implications. *Seminar on Reproduction Endobrinology*, 17(4), pp. 327-38.
22. Craig 1W. (2005). The role of monoamine oxidase A, MAOA, in the aetiology of antisocial behaviour: the importance of gene-environment interactions. *Novartis Found Symp* 268, pp. 227-237.
23. Cohen IL, Liu X, Schutz C, White BN, Jenkins EC, Brown WT, & Holden JJ. (2003, September). Association of autism severity with a monoamine oxidase A functional polymorphism. Clin Genet 64(3), pp. 190-197.
24. Davis LK, Hazlett HC, Librant AL, Nopoulos P, Sheffield VC, Piven J, & Wassink TH. (2008 Oct. 5). Cortical enlargement in autism is associated with a functional VNTR in the monoamine oxidase A gene. *Am J Med Genet B Neuropsychiatr Genet* 1478(7), pp. 1145-1151.
25. Courchesne E, Carper R, & Akshoomoff N. (2003 Jul. 16). Evidence of brain overgrowth in the first year of life in autism. *JAMA* 290(3), pp. 337-344.
26. Continni V. Marques FZ, Garcia CE, Hutz MH, & Bau CH. (2006 Apr. 5). MAOA-uVNTR polymorphism in a Brazilian sample: further support for the association with impulsive behaviors and alcohol dependence. *Am J Med Genet B Neuropsychiatry Genet* 141B(3), pp. 305-308.
27. Dziobek I, Gold SM, Wolf OT, & Convit A. (2007 Jan. 15). Hypercholesteremia in Asperger syndrome: independence from lifestyle, obsessive-compulsive behavior, and social anxiety. *Psychiatry Res* 149 (1-3), pp. 321,324.
28. Brummett BH, Boyle SH, Siegler IC, Zuchner S, Ashley-Kock A, & Williams RB. (2008, February). Lipid levels are associated with a regulatory polymorphism of the monoamine oxidase-A gene promoter (MAOA-uVNTR). *Med Sci Monit* 14(2), pp. 57-61.
29. Heron P, Cousins K, Boyd C, & Daya S. (2001 Feb. 23). Paradoxical effects of copper and manganese on brain mitochondrial function. *Life-Sci* 68(14), pp. 1575-1583.
30. Cakala M, Drabik J, Kaz mierczak A, Kopczuk D, & Adamczyk A. (2006). Inhibition of mitochondrial complex II affects dopamine metabolism and decreases its uptake into striatal synaptosomes. *Folia Neuropathol* 44(4), pp. 238-243.
31. McNamara IM, Borelia AW, Bialowas LA, & Whitaker-Azmitia PM. (2008 Jan. 16). Further studies in the development hyperserotonemia model (DHS) of autism: social behavioral and peptide changes. *Brain Res* 1189, pp. 203-214
32. Youdim, MBH & Sandler M. (1968). Activation of monoamine oxidae and inhibition of aldehyde dehyrogenase by reserpine. *European Journal of Pharmacology*, 4, pp. 105-108.
33. Vijayalakshmi V., Lel JV, & Daginawala HF. (1978). Effect of reserpine on the monoamine oxidase (MAO) activity in rat lever and brain. *Biochemical Pharmacology*, 27(15), pp. 1985-1986.
34. Thatcher, RW, Walker, RA, Biver, CJ, North, DM, & Curtin R. (2003). Sensitivity and Specificity of an EEG Normative Database: Validation and Clinical correlation. *J. Neurotherapy*, 7(No. 3/4), pp. 87-122.
35. Rossignol DA, Rossignol LW, James SJ, Melnyk S, & Mumper E. (1007, November). The effects of hyperbaric oxygen therapy on oxidative stress, inflammation, and symptoms in children with autism: an open-label pilot study. *BMC Pediatr* 16, pp. 7-36.
36. Lehman E, Haber J, & Lesser S. (1957, July-September). The Use of Reserpine in Autistic Children. *The Journal of Nervous and Mental Disease*, 125(3), pp. 351-356.
37. MacReady N. (2001 Jun. 1). Promising New Antipsychotics for Pediatric Patients (clozapine, reserpine, olanzapine, quetiapine). Clinical psychiatry News.

What is claimed is:

1. A method for treatment of the symptoms of an autism spectrum disorder, comprising;
    administering to a patient daily a 12C homeopathic dilution of reserpine by transdermal administration.
2. The method of claim 1, wherein the step of administering to a patient daily a 12C homeopathic dilution of reserpine by transdermal administration comprises:
    administering to a patient a 12C homeopathic dilution of reserpine having reserpine as a sole active ingredient.
3. A method for treatment of the symptoms of an autism spectrum disorder, comprising:
    administering to a patient daily a 12C homeopathic dilution of reserpine by transdermal administration, said homeopathic dilution of reserpine having reserpine as a sole active ingredient.

* * * * *